(12) United States Patent
Miyai et al.

(10) Patent No.: US 9,786,057 B2
(45) Date of Patent: Oct. 10, 2017

(54) INSPECTION APPARATUS, COORDINATE DETECTION APPARATUS, COORDINATE DETECTION METHOD, AND WAVEFRONT ABERRATION CORRECTION METHOD

(71) Applicant: Lasertec Corporation, Yokohama, Kanagawa (JP)

(72) Inventors: Hiroki Miyai, Yokohama (JP); Masafumi Shinoda, Yokohama (JP)

(73) Assignee: Lasertec Coporation, Yokohama (JP)

( * ) Notice: Subject to any disclaimer, the term of this patent is extended or adjusted under 35 U.S.C. 154(b) by 140 days.

(21) Appl. No.: 14/837,229

(22) Filed: Aug. 27, 2015

(65) Prior Publication Data

US 2016/0088213 A1    Mar. 24, 2016

(30) Foreign Application Priority Data

Sep. 19, 2014 (JP) .................................. 2014-190963
Oct. 20, 2014 (JP) .................................. 2014-213996

(51) Int. Cl.
*G06K 9/00* (2006.01)
*G06T 7/00* (2017.01)
(Continued)

(52) U.S. Cl.
CPC ....... *G06T 7/0085* (2013.01); *G01N 21/9501* (2013.01); *G01N 21/956* (2013.01);
(Continued)

(58) Field of Classification Search
CPC ..... G06T 7/0042; G06T 7/0085; G06T 7/001; G06T 2207/30148; G06K 9/4661;
(Continued)

(56) References Cited

U.S. PATENT DOCUMENTS 6,900,435 B1    5/2005 Lewis
9,445,003 B1*   9/2016 Lelescu ............ H04N 5/23232
(Continued)

FOREIGN PATENT DOCUMENTS

JP    56048510 A    5/1981
JP    63061905 A    3/1988
(Continued)

OTHER PUBLICATIONS

Japanese Patent Office, Office Action Issued in Japanese Patent Application No. 2014-213996, Nov. 4, 2015, 6 pages. (Submitted with Partial Translation).

(Continued)

*Primary Examiner* — Amir Alavi
(74) *Attorney, Agent, or Firm* — McCoy Russell LLP

(57) ABSTRACT

In an inspection apparatus according to one aspect of the present invention, a processing apparatus includes: a profile data generation unit that divides each of a plurality of images according to a circumferential position to generate profile data in which a radial direction position and luminance data are associated with each other; a deconvolution operation unit that carries out a deconvolution operation using a one-dimensional point spread function to generate deconvolution operation data based on the profile data; an estimation unit that estimates estimation data of the deconvolution operation data in a desired focus position in the optical axis direction using the deconvolution operation data; and a synthesis unit that synthesizes the estimation data estimated by the estimation unit for each radial direction position to generate the image in the desired focus position.

12 Claims, 17 Drawing Sheets

(51) Int. Cl.
*H04N 5/225* (2006.01)
*G01N 21/95* (2006.01)
*G01N 21/956* (2006.01)
*G03F 1/84* (2012.01)

(52) U.S. Cl.
CPC .............. *G03F 1/84* (2013.01); *H04N 5/2256* (2013.01); *G01N 2021/95676* (2013.01)

(58) Field of Classification Search
CPC ............. G06K 9/4604; H04N 5/23212; H04N 5/2256; G03F 1/84; G03F 1/144; G01N 21/95607
See application file for complete search history.

(56) References Cited

U.S. PATENT DOCUMENTS

| | | | |
|---|---|---|---|
| 2009/0244513 A1 | 10/2009 | Matsumoto et al. | |
| 2013/0088489 A1* | 4/2013 | Schmeitz | H04N 5/2254 345/419 |
| 2013/0245971 A1 | 9/2013 | Kusunose et al. | |
| 2014/0031689 A1* | 1/2014 | Kang | G01S 15/8977 600/443 |
| 2014/0168035 A1* | 6/2014 | Luebke | G02B 27/017 345/8 |
| 2016/0088213 A1* | 3/2016 | Miyai | H04N 5/2256 348/349 |
| 2016/0110499 A1* | 4/2016 | Donnet | G06F 19/22 506/2 |

FOREIGN PATENT DOCUMENTS

| | | |
|---|---|---|
| JP | H01251176 A | 10/1989 |
| JP | 2002536696 A | 10/2002 |
| JP | 2005019544 A | 1/2005 |
| JP | 2005083795 A | 3/2005 |
| JP | 2006279359 A | 10/2006 |
| JP | 2008181778 A | 8/2008 |
| JP | 2009239077 A | 10/2009 |
| JP | 2013191733 A | 9/2013 |

OTHER PUBLICATIONS

Japanese Patent Office, Office Action Issued in Japanese Patent Application No. 2014-213996, Jun. 23, 2015, 7 pages.

* cited by examiner

INSPECTION APPARATUS, COORDINATE DETECTION APPARATUS, COORDINATE DETECTION METHOD, AND WAVEFRONT ABERRATION CORRECTION METHOD

INCORPORATION BY REFERENCE

This application is based upon and claims the benefit of priority from Japanese patent applications No. 2014-190963, filed on Sep. 19, 2014, and No. 2014-213996, filed on Oct. 20, 2014, the disclosures of which are incorporated herein in their entireties by reference.

BACKGROUND OF THE INVENTION

1. Field of the Invention

The present invention relates to an inspection apparatus, a coordination detection apparatus, a coordination detection method and a wavefront aberration correction method.

2. Description of Related Art

Published Japanese Translation of PCT International Publication for Patent Application, No. 2002-536696 discloses a method for performing a deconvolution operation on data captured by a scanned probe microscope. A point spread function is used in the deconvolution operation. By using the point spread function, it is possible to prevent diffraction of a lens, aberration of the lens and the like from influencing an image.

In recent years, Extremely Ultraviolet Lithography (EUVL) having a wavelength of 13.5 nm has been developed in order to achieve miniaturization of semiconductor patterns. Therefore, an actinic inspection apparatus that uses 13.5 nm Extremely Ultraviolet (EUV) light as illumination light has been developed. The optical system of the EUV light uses a multi-layer film reflection optical system having a reflection surface on which a multi-layer film is formed. In a light collecting optical system, for example, a concave mirror has been used in place of a lens.

In the inspection apparatus using the EUV light, in order to inspect fine patterns or the like, observation at a high magnification and high numerical aperture (NA) is desired. However, an aberration occurs due to the occurrence of a positional error or a manufacturing error of the mirror with the multi-layer film. The observed image is blurred due to the aberration. In order to reduce the occurrences of such an aberration, high-accuracy mirror polishing is required, which causes an increase in the manufacturing cost. Further, in order to secure a resolution of 100 nm or smaller in magnifying observation using the EUV multi-layer film reflector, it is required to suppress wavefront aberration and to polish the reflection surface with extremely high accuracy.

Further, when the multi-layer reflection optical system in which the working distance is about 20 mm or larger and NA is above 0.2 to enable an arrangement of various optical components is used, it is difficult to manufacture such a multi-layer reflection optical system since the mirror diameter is large. That is, when the large-sized curved mirror is used, it is difficult to process such a curved mirror with high accuracy. This causes blurring in the optical image due to wavefront aberration.

The present invention has been made in view of the above circumstances and aims to provide an inspection apparatus and a wavefront aberration correction method capable of suppressing fuzziness of an optical image due to wavefront aberration.

Another problem is described hereinbelow. When a defect mitigation is carried out in the EUVL, a pattern of an absorber is formed to cover the defect. It is therefore possible to hide the defect by the pattern of the absorber, whereby it is possible to prevent the defect from being transferred into a wafer.

As described above, in order to carry out the defect mitigation, after an EUV mask blanks is inspected, the pattern of the absorber of the EUV mask is formed in the blanks by an EB drawing apparatus. In order to cover the defect with the pattern of the absorber, it is required to detect the defect with high position accuracy. Accordingly, it is required in the defect inspection apparatus to carry out the alignment with high position accuracy.

Typically, an alignment mark (fiducial mark) is used in the alignment of the mask. For example, the fiducial mark is detected with high position accuracy to inspect the defect. By using the fiducial mark as reference coordinates, the coordinates of the defect may be detected with high position accuracy.

Typically, a cross pattern is used as the fiducial mark (Japanese Unexamined Patent Application Publication No. 2005-83795). The cross pattern is formed, for example, by forming a groove. It is technically required to accurately detect the fiducial mark with high repeatability in order to increase the accuracy of the position of the coordinates of the defect. When an image is blurred, however, the fiducial mark may not be detected with high detection accuracy.

The present invention has been made in view of the above circumstances and aims to provide a coordinate detection apparatus, an inspection apparatus, and a coordinate detection method capable of accurately detecting coordinates.

SUMMARY OF THE INVENTION

An inspection apparatus according to a first aspect of an embodiment includes: an illumination light source that generates illumination light, the illumination light illuminating a sample; an image capture unit that captures a plurality of images of the sample in different focus positions in an optical axis direction; and a processing apparatus that generates an image in a desired focus position in the optical axis direction based on the plurality of images, in which the processing apparatus includes: a profile data generation unit that divides each of the plurality of images according to a circumferential position to generate profile data in which a radial direction position and luminance data are associated with each other; a deconvolution operation unit that carries out a deconvolution operation using a one-dimensional point spread function to generate deconvolution operation data based on the profile data; an estimation unit that estimates estimation data of the deconvolution operation data in the desired focus position in the optical axis direction using the deconvolution operation data; and a synthesis unit that synthesizes the estimation data estimated by the estimation unit for each radial direction position to generate the image in the desired focus position.

In the above inspection apparatus, the processing apparatus may calculate a shift amount of a peak position of the deconvolution operation data or the profile data and the estimation unit may shift the deconvolution operation data in a radial direction based on the shift amount to estimate the estimation data.

The above inspection apparatus may include: carrying out, by the deconvolution operation unit, the deconvolution operation on the profile data at each of the different focus positions to generate a plurality of pieces of deconvolution operation data; calculating a peak position of each of the plurality of pieces of deconvolution operation data; and shifting the deconvolution operation data in the radial direction based on the shift amount of the peak position of each of the plurality of pieces of deconvolution operation data to calculate the estimation data.

The above inspection apparatus may include: carrying out a convolution operation using two pieces of profile data having different focus positions to generate convolution operation data; obtaining a shift amount of a peak position of each of the two pieces of profile data based on the convolution operation data; shifting one of the two pieces of profile data in the radial direction based on the shift amount; and carrying out, by the deconvolution operation unit, the deconvolution operation on the square root of the product of one piece of the profile data shifted in the radial direction and the other pieces of profile data to generate the deconvolution operation data.

In the above inspection apparatus, at least one curved mirror may be provided in an optical system that propagates scattered light from the sample to the image capture unit and the curved mirror may project the sample on the image capture unit in a magnified manner.

In the above inspection apparatus, the illumination light is preferably EUV light.

A wavefront aberration correction method according to a first aspect of an embodiment is a wavefront aberration correction method in which a processing apparatus generates an image in a desired focus position in an optical axis direction based on a plurality of images captured in different focus positions in the optical axis direction, in which the step of generating the image includes: dividing each of the plurality of images according to a circumferential position to generate profile data in which a radial direction position and luminance data are associated with each other; carrying out a deconvolution operation using a one-dimensional point spread function to generate deconvolution operation data based on the profile data; estimating estimation data of the deconvolution operation data in the desired focus position in the optical axis direction using the deconvolution operation data; and synthesizing the estimation data estimated by the estimation unit for each radial direction position to generate the image in the desired focus position.

The above wavefront aberration correction method may include: calculating a shift amount of a peak position of the deconvolution operation data or the profile data; and shifting the deconvolution operation data in a radial direction based on the peak position to estimate the estimation data.

The above wavefront aberration correction method may include: carrying out the deconvolution operation on the profile data at each of the different focus positions to generate a plurality of pieces of deconvolution operation data; calculating a peak position of each of the plurality of pieces of deconvolution operation data; and shifting the deconvolution operation data in the radial direction based on the shift amount of the peak position of each of the plurality of pieces of deconvolution operation data to calculate the estimation data.

The above wavefront aberration correction method may include: carrying out a convolution operation using two pieces of profile data having different focus positions to generate convolution operation data; obtaining a shift amount of a peak position of each of the two pieces of profile data based on the convolution operation data; shifting one of the two pieces of profile data in the radial direction based on the shift amount; and carrying out, by the deconvolution operation unit, the deconvolution operation on the square root of the product of one piece of the profile data shifted in the radial direction and the other pieces of profile data to generate the deconvolution operation data.

In the above wavefront aberration correction method, at least one curved mirror may be provided in an optical system that propagates scattered light from the sample to the image capture unit and the curved mirror may project the sample on the image capture unit in a magnified manner.

In the above wavefront aberration correction method, the illumination light that illuminates the sample is preferably EUV light.

According to the present invention, it is possible to provide an inspection apparatus and a wavefront aberration correction method capable of suppressing fuzziness of an optical image due to wavefront aberration.

The above and other objects, features and advantages of the present invention will become more fully understood from the detailed description given hereinbelow and the accompanying drawings which are given by way of illustration only, and thus are not to be considered as limiting the present invention.

DESCRIPTION OF THE EXEMPLARY EMBODIMENTS

A description is hereinafter made of specific configurations of embodiments with reference to the drawings. It should be noted that the following description describes preferable embodiments of the present invention and the present invention is not limited to the following embodiments. In the following description, components denoted by the same reference symbols are substantially the same.

First Embodiment

Figure 1:
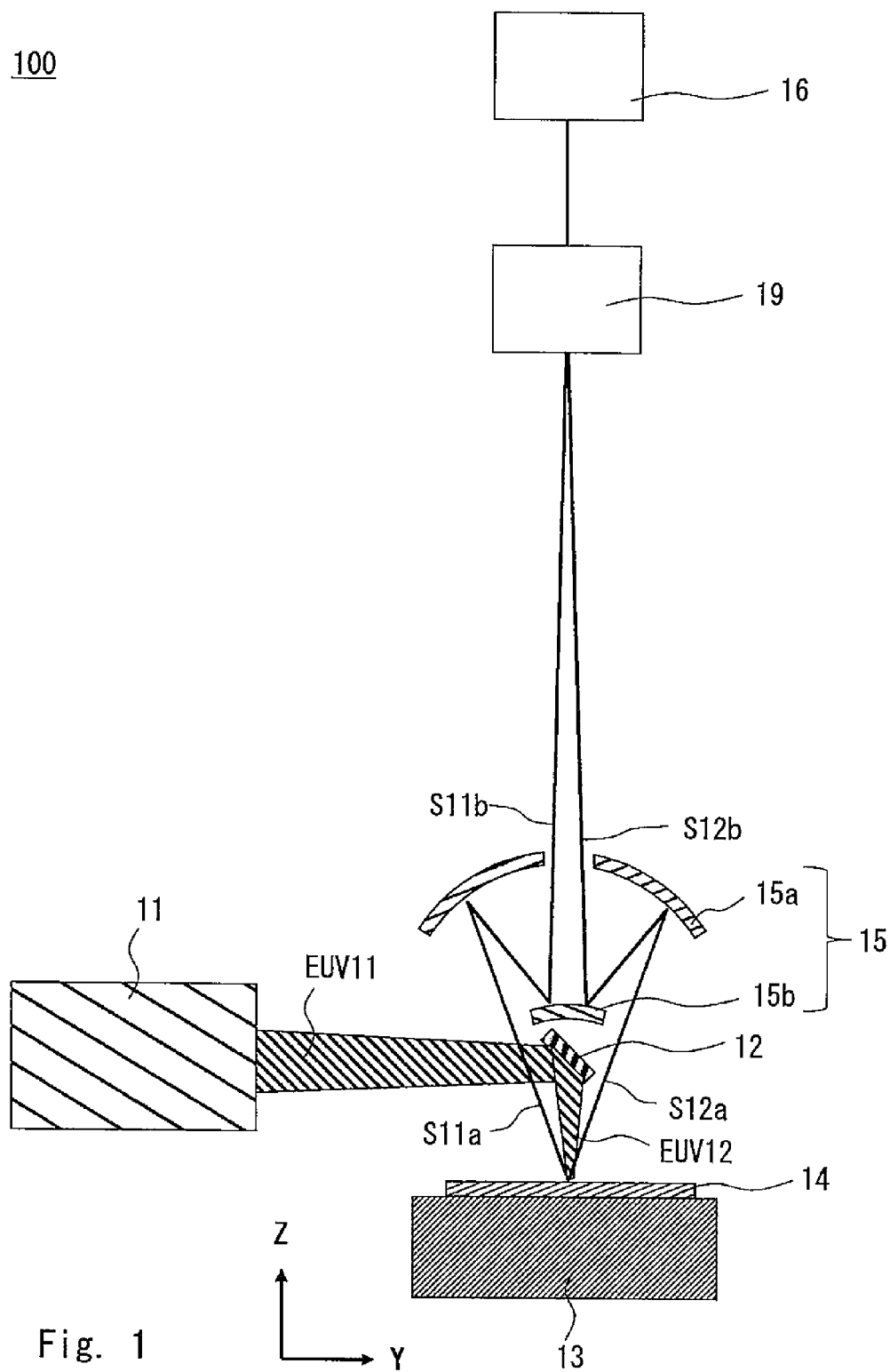
FIG. 1 is a diagram showing a configuration of an inspection apparatus according to this embodiment.

With reference to FIG. 1, a configuration of an inspection apparatus according to this embodiment will be described. FIG. 1 is a diagram showing a configuration of an inspection apparatus 100 that detects defects of a sample. The object to be inspected is, for example, a patterned mask for EUV lithography, a mask blank, a mask substrate or the like and is hereinafter referred to as a mask 14. Further, the inspection apparatus 100 is also able to inspect an object other than the mask (e.g., a semiconductor device). The inspection apparatus 100 carries out an actinic inspection using 13.5 nm EUV light. That is, the inspection apparatus 100 inspects the mask 14 using an illumination wavelength the same as an exposure wavelength (13.5 nm) in a lithography process. Further, by using the EUV light, observation at high resolution becomes possible. For example, the inspection apparatus 100 is able to capture images at the magnifying observation of 1200 times and the resolution of 100 nm or smaller.

The inspection apparatus 100 includes an illumination apparatus 11, a multi-layer film plane mirror 12, a Schwarzschild expansion optical system 15, a processing apparatus 16, and a TDI camera 19. The Schwarzschild expansion optical system 15 is constituted of a concave mirror 15a with a hole and a convex mirror 15b. In FIG. 1, for the sake of clarification of the description, the direction perpendicular to the plane of the mask 14 is denoted by a Z direction and the direction parallel to the paper on the plane parallel to the plane of the mask 14 is denoted by a Y direction. The Z direction is parallel to the optical axis of the Schwarzschild expansion optical system 15. As will be described later, the direction perpendicular to the Y direction on the plane parallel to the plane of the mask 14 are denoted by an X direction.

The illumination apparatus 11 generates, for example, 13.5 nm EUV light EUV11, which has the same wavelength as the exposure wavelength. That is, the illumination apparatus 11 is an illumination light source. The EUV light EUV11 generated in the illumination apparatus 11 advances while being contracted. The EUV light EUV11 impinges on the multi-layer film plane mirror 12 and reflects downwardly. An EUV light EUV12 reflected in the multi-layer film plane mirror 12 is made incident on the mask 14. The multi-layer film plane mirror 12 is a drop-down mirror that is arranged immediately above the mask 14 and reflects the EUV light EUV12 toward the mask 14.

The EUV light EUV12 illuminates a minute inspection region in the mask 14 placed on a stage 13. This inspection region has a size of about 0.5 mm square. When there is a defect in this minute region, scattered light is generated. For example, scattered light S11a and S12a generated due to a minute defect are reflected in the concave mirror 15a with the hole and the convex mirror 15b, advance as scattered light S11b and S12b, respectively, and reach the TDI camera 19.

More specifically, the scattered light S11a and S12a from the mask 14 are made incident on the concave mirror 15a with the hole. The scattered light reflected by the concave mirror 15a with the hole is made incident on the convex mirror 15b. The scattered light S11b and 12b reflected by the convex mirror 15b pass through the hole provided at the center of the concave mirror 15a with the hole and are then made incident on the TDI camera 19. The TDI camera 19 captures a magnified image of the mask 14. According to this operation, the defect on the surface of the mask 14 is detected. As a matter of course, the magnified image may be captured by a typical CCD camera or a photodetector instead of using the TDI camera 19.

As described above, the concave mirror 15a with the hole and the convex mirror 15b are provided in the Schwarzschild expansion optical system 15 through which the EUV light propagates. The concave mirror 15a with the hole and the convex mirror 15b are multi-layer film curved mirrors each having a multi-layer film formed on its surface. The Schwarzschild expansion optical system 15 projects the mask 14 on the TDI camera 19 in an enlarged manner by the curved mirrors such as the concave mirror 15a with the hole, the convex mirror 15b and the like. Accordingly, the TDI camera 19 captures the optical image of the mask 14.

An output signal from the TDI camera 19 is input to the processing apparatus 16. The processing apparatus 16 carries out an inspection of defects in the mask 14 according to the output signal from the TDI camera 19. The processing apparatus 16 includes an inspection circuit to detect the defect. For example, the processing apparatus 16 compares a detection value detected by the TDI camera 19 with a threshold to detect the defect based on the result of comparison. Further, the processing apparatus 16 executes a deconvolution operation on the image captured by the TDI camera 19 to suppress fuzziness of the optical image due to wavefront aberration. This deconvolution operation will be described later.

The multi-layer film plane mirror 12 for illumination is provided between the concave mirror 15a with the hole and the mask 14. Further, the scattered light S11a and the scattered light S12a are shown as scattered light beams which are made incident on the sides opposite to each other with the hole of the concave mirror 15a interposed therebetween. More specifically, the scattered light that is made incident on the right side of the hole provided in the concave mirror 15a is denoted by the scattered light S12a and the scattered light that is made incident on the left side of the hole provided in the concave mirror 15a is denoted by the scattered light S11a.

The stage 13 is an XYZ stage and is movable in the XYZ directions. For example, the stage 13 moves in the XY directions, whereby it is possible to capture a desired position of the mask 14. Further, the stage 13 moves in the Z direction, whereby it is possible to capture the mask 14 at an arbitrary height. For example, the focus position in the optical axis direction can be varied by moving the stage 13. The focus position may also be changed by moving at least one of the TDI camera 19, the concave mirror 15*a* with the hole, and the convex mirror 15*b* in the optical axis direction, not only by moving the stage 13.

While the light scattered in the mask 14 is detected through the Schwarzschild expansion optical system 15 that is constituted of the concave mirror 15*a* with the hole and the convex mirror 15*b* in FIG. 1, besides the Schwarzschild expansion optical system 15, a concave mirror or a plane mirror may be further provided in the inspection apparatus 100.

The inspection apparatus 100 carries out dark-field illumination observation using the Schwarzschild expansion optical system 15. The EUV light EUV12 reflected in the multi-layer film plane mirror 12 illuminates the mask 14 and the scattered light EUV light S11 and S12 from the mask 14 that have passed through the outside of the multi-layer film plane mirror 12 are detected by the TDI camera 19 through the Schwarzschild expansion optical system 15. When such a dark-field illumination optical system is used, the angle distribution of the scattered light intensity differs depending on the target to be observed. That is, the scattering directions become asymmetric and each scattering angle direction has a different scattered light intensity. For example, when there is a defect in the mask 14, the intensity of the scattered light S11*a* becomes different from the intensity of the scattered light S12*a* according to the shape or the like of the defect.

In such a case, it is difficult to accurately reproduce the image by the deconvolution operation using a two-dimensional point spread function. In order to solve this problem, in this embodiment, the processing apparatus 16 carries out a deconvolution operation using a one-dimensional point spread function. The processing apparatus 16 calculates the image in the focusing position from a plurality of images acquired in non-focal positions. The processing apparatus 16 is an arithmetic processing unit such as a personal computer and includes a memory, a central processing unit (CPU) and the like. For example, the processor reads out and executes a program stored in the memory or the like to execute predetermined processing. According to this operation, a deconvoluted image in which wavefront aberration is suppressed is generated.

Figure 2:
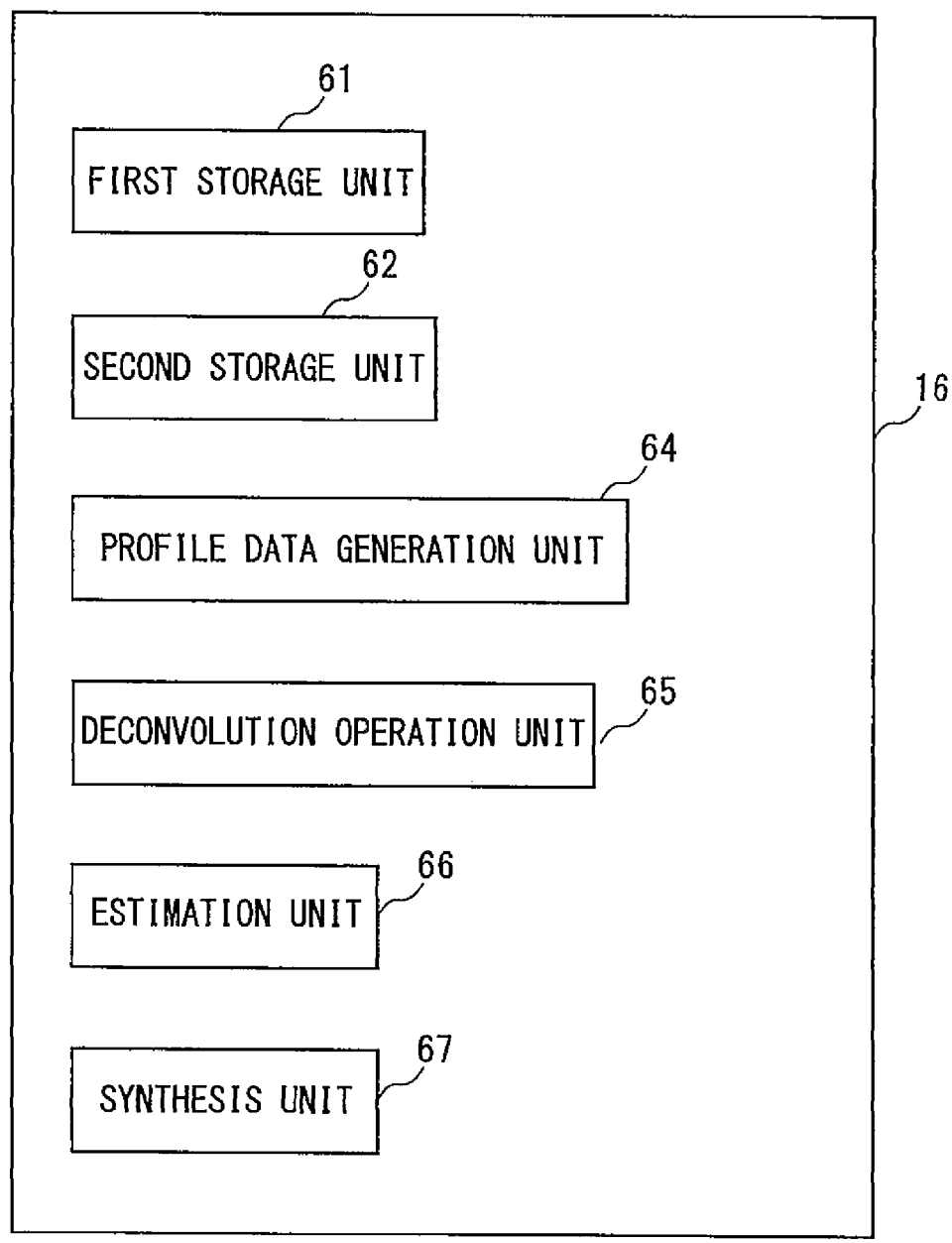
FIG. 2 is a block diagram showing a configuration of a processing apparatus used in the inspection apparatus.

In the following description, with reference to FIGS. 2 to 7, wavefront aberration correction processing by the processing apparatus 16 will be described. FIG. 2 is a block diagram showing a configuration of the processing apparatus 16. FIGS. 3 to 7 are diagrams for describing the processing in the processing apparatus 16.

The processing apparatus 16 includes a first storage unit 61, a second storage unit 62, a profile data generation unit 64, a deconvolution operation unit 65, an estimation unit 66, and a synthesis unit 67.

The first storage unit 61 and the second storage unit 62 store images of the mask 14 captured by the TDI camera 19. The first storage unit 61 and the second storage unit 62 store the XY positions in the mask 14 and luminance data F in association with each other. That is, the first storage unit 61 and the second storage unit 62 store F(x,y). Note that x indicates the position in the X direction (X coordinate) and y indicates the position in the Y direction (Y coordinate).

Further, the first storage unit 61 and the second storage unit 62 store images in different Z positions. In the following description, as shown in FIG. 3, the image stored in the first storage unit 61 is denoted by a first image in Z=Z1 and the image stored in the second storage unit 62 is denoted by a second image in Z=Z2.

Z1 and Z2 of the Schwarzschild expansion optical system 15 are Z positions which are out of focus, that is, non-focal positions. For example, the first image is an image deviated from the focusing position by Z1 and the second image is an image deviated from the focusing position by Z2. Z2 is larger than Z1. Further, the Z position where the Schwarzschild expansion optical system 15 is focused, which is a focusing position, is assumed to be Z=Z0. While the image in the focal position is shown in FIG. 3, the TDI camera 19 may not acquire the image in the focal position. That is, the TDI camera 19 may capture at least two images in the non-focal positions. In this embodiment, the processing apparatus 16 obtains the deconvoluted image in Z=Z0 based on the images in Z=Z1, Z2.

Figure 3:
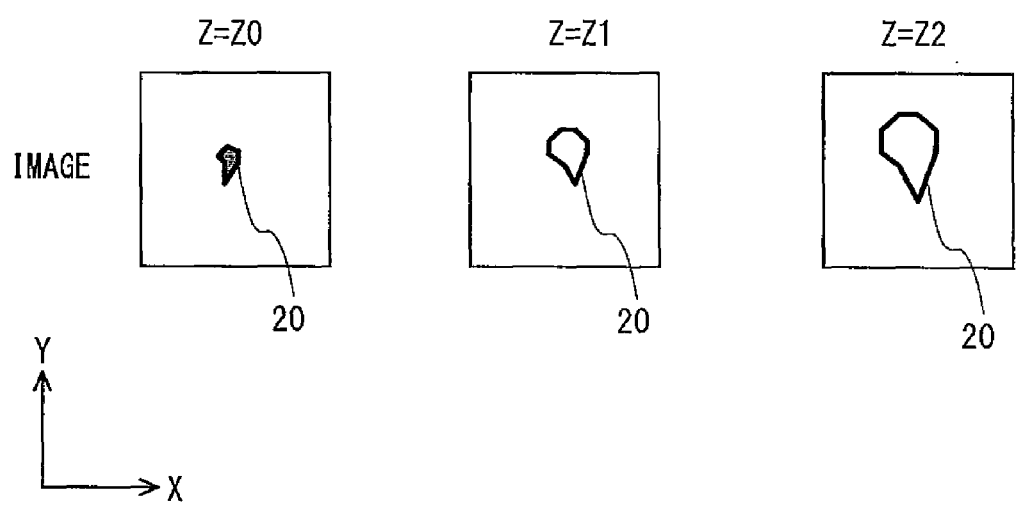
FIG. 3 is a diagram schematically showing a plurality of images acquired in the inspection apparatus.

In FIG. 3, in Z=Z0, there is a defect 20 at the center of the image. By shifting the focus position from the focusing position, the defect 20 is blurred. Z1 is located closer to the focusing position (Z=X0) than Z2 is. Accordingly, the defect 20 is more blurred in the second image in Z=Z2 than in the first image in Z=Z1. In this embodiment, the processing apparatus 16 carries out the following processing on the image having the defect 20 at the center thereof.

As stated above, in the first and second images, the XY positions (XY coordinates) and the luminance data are associated with each other. The profile data generation unit 64 generates one-dimensional profile data in the radial direction of the first and second images. Accordingly, first, the profile data generation unit 64 carries out coordinate transformation on the first and second images. The profile data generation unit 64 transforms the coordinate system of the image data from the XY rectangular coordinate system to a polar coordinate system. The radial direction position is denoted by r and the circumferential position is denoted by θ. The profile data generation unit 64 converts F(x,y) into F(r,θ). Since the intensity of the scattered light varies according to the scattering angle, the XY rectangular coordinate system is converted into the polar coordinates. The radial direction (r direction) and the circumferential direction (θ direction) are perpendicular to each other.

Figure 4:
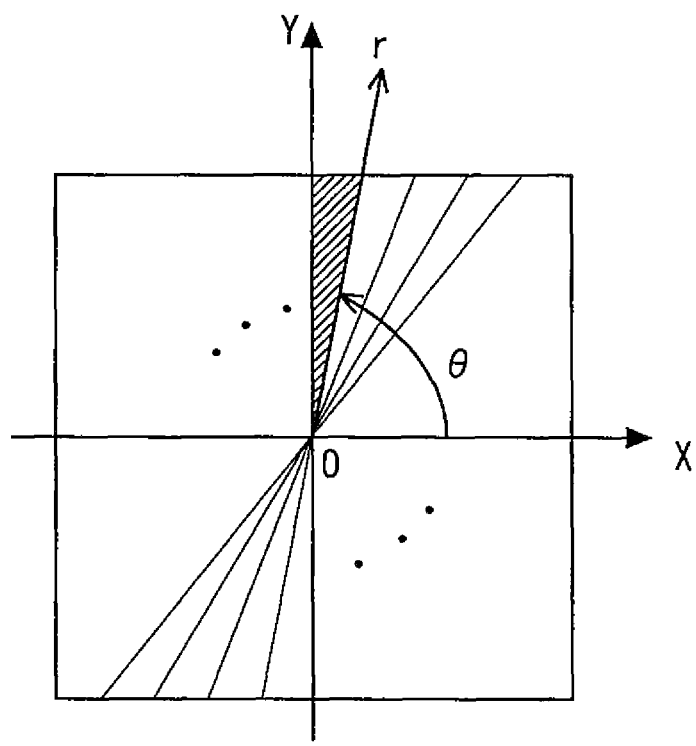
FIG. 4 is a diagram for describing image coordinate transformation processing.

The profile data generation unit 64 generates profile data Fn(r) in the r direction based on F(r,θ). For example, the profile data generation unit 64 integrates Fn(r,θ) for each particular angle component. As shown in FIG. 4, the profile data generation unit 64 radially divides the image. The profile data generation unit 64 integrates luminance data for each angle component to generate the profile data Fn(r) in the r direction. The profile data generation unit 64 generates the profile data for all directions. The profile data generation unit 64 divides the image for each θn<θ<θn+1 (n is an integer of two or larger) to express the luminance data by a function of only r. The profile data Fn(r) is obtained, for example, based on the following Expression (1).

$$F_n(r) = \int_{\theta_n}^{\theta_{n+1}} F(r,\theta) d\theta \quad (1)$$

Figure 5:
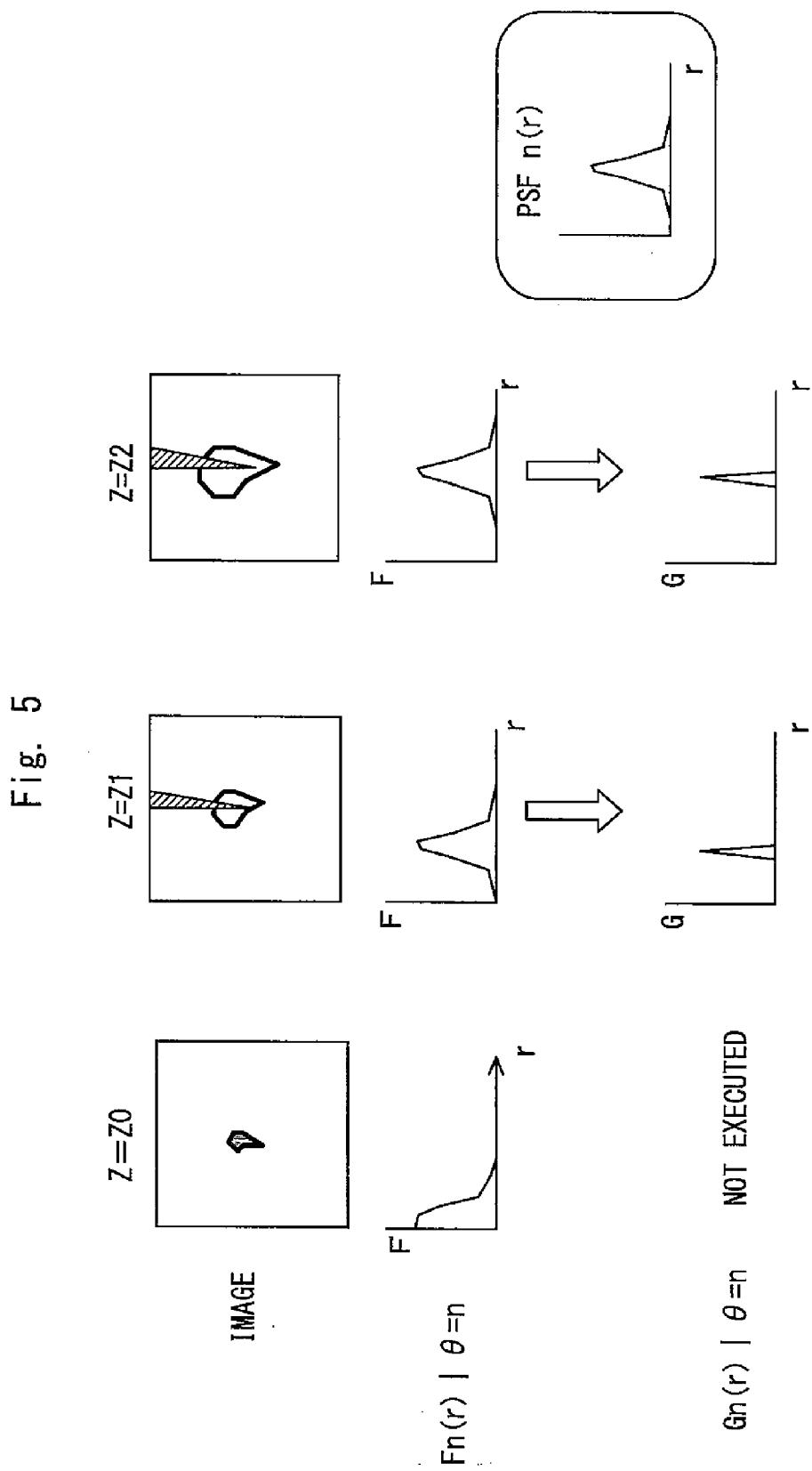
FIG. 5 is a diagram showing profile data and deconvolution operation data in an r direction.

FIG. 5 shows profile data Fn(r)|θ=n when θn<θ<θn+1. Since the polar coordinate transformation has been carried out, r is a value of 0 or larger. In Z=Z0, Z1, Z2, the r coordinate of the peak of the profile data Fn(r)|θ=n is deviated. The blurring of the image becomes larger as the distance from the focusing position increases. Therefore, the peak position moves to the outside as the distance from the focusing position increases. Since the defect is at the center of the image in the focusing position, the peak is located at around r=0. Then, the r coordinate of the peak increases as the deviation in the Z direction from the focusing position increases.

As described above, the profile data generation unit 64 divides the image according to the circumferential position to calculate the profile data Fn(r). The profile data generation unit 64 calculates a plurality of pieces of profile data based on the first image, where n=1, 2, . . . n. In a similar way, the profile data generation unit 64 calculates the plurality of pieces of profile data based on the second image. As stated above, the profile data generation unit 64 generates the profile data in the r direction for each circumferential position.

The profile data generation unit 64 carries out the same processing on the first and second images to generate the profile data Fn(r). Accordingly, the number of profile data Fn(r)|Z=Z1 that the profile generation unit 64 generates for the first image is the same as the number of profile data Fn(r)|Z=Z2 that it generates for the second image. In the profile data, the radial direction position (r coordinate) and the luminance data are associated with each other. Since the Z direction position is the non-focal position in Z=Z1 and Z=Z2, the profile data is out-of-focus profile data.

The deconvolution operation unit 65 carries out the deconvolution operation using the one-dimensional point spread function, thereby generating deconvolution operation data based on the profile data. The one-dimensional point spread function PSFn(r) shown in FIG. 5 is set in the deconvolution operation unit 65. In the point spread function PSFn(r), the radial direction position (r) and the intensity are associated with each other.

The point spread function PSFn(r) differs for each circumferential position. That is, the point spread function PSFn(r) differs for each n. Further, the point spread function PSFn(r) in the first image is the same as that in the second image. That is, the deconvolution operation unit 65 carries out the deconvolution operation using the same point spread function PSFn(r) for all the images.

As described above, the deconvolution operation unit 65 executes the deconvolution operation on Fn(r). According to this operation, the deconvolution operation unit 65 generates deconvolution operation data Gn(r) as shown in FIG. 5. As described above, the deconvolution operation unit 65 generates the deconvolution operation data Gn(r) by performing a one-dimensional deconvolution operation on the profile data Fn(r). The deconvolution operation data is, similar to the profile data, data in which the radial direction position and the luminance data are associated with each other. The deconvolution operation is not executed in the profile data Fn(r)|Z=Z0 of the focusing position.

The deconvolution operation data Gn(r) is calculated for each of the first image and the second image. That is, the deconvolution operation unit 65 calculates the deconvolution operation data Gn(r)|Z=Z1 in Z=Z1 and the deconvolution operation data Gn(r)|Z=Z2 in Z=Z2. Further, the deconvolution operation unit 65 calculates the deconvolution operation data for each θ. That is, the deconvolution operation unit 65 executes the deconvolution operation on the profile data in each circumferential position.

The estimation unit 66 estimates the deconvoluted image in the focusing position based on the result of an operation in the deconvolution operation unit 65. The estimation unit 66 estimates the deconvoluted image in the focusing position using the deconvolution operation data Gn(r) in Z=Z1, Z2. Accordingly, the estimation unit 66 estimates the estimation data of the deconvolution operation data in the focusing position. Note that the estimation data is data in which the radial direction position and the luminance data are associated with each other.

Figure 6:
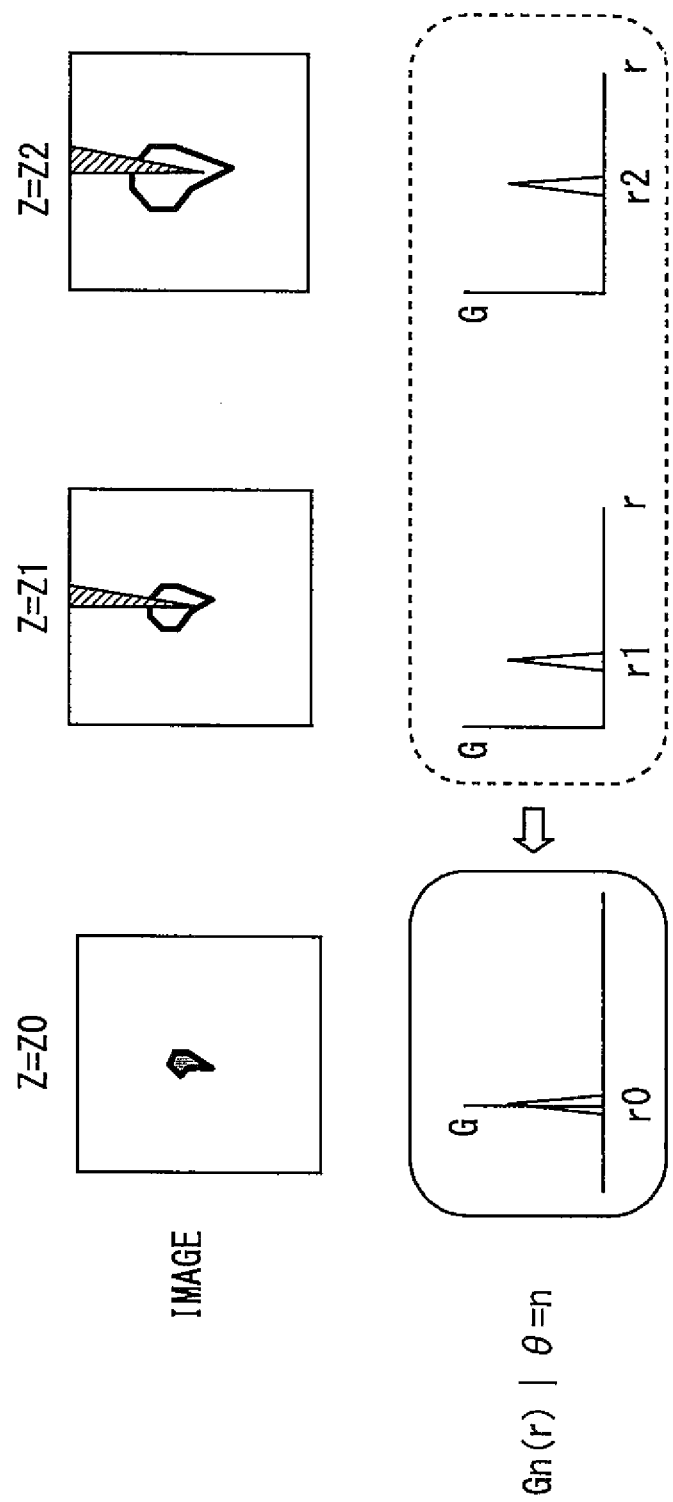
FIG. 6 is a diagram for describing processing for estimating deconvolution operation data in a focusing position using deconvolution operation data.

In this embodiment, the estimation unit 66 estimates the estimation data by a linear interpolation. Specifically, as shown in FIG. 6, the estimation unit 66 calculates a peak position r1 of the deconvolution operation data Gn(r)|Z=Z1. In a similar way, the estimation unit 66 calculates a peak position r2 of the deconvolution operation data Gn(r)|Z=Z2. The estimation unit 66 calculates, for example, the local maximum value or the maximum value of the deconvolution operation data Gn(r) as the peak position.

The estimation unit 66 calculates a peak position r0 of the deconvolution operation data in the focusing position (Z=Z0) by the linear interpolation from the peak position r1 and the peak position r2. The estimation unit 66 offsets r, assuming that the shape of Gn(r) does not change even when the Z coordinate varies. According to such an operation, the estimation unit 66 calculates the estimation data of the deconvolution operation data of Z=Z0. That is, the estimation unit 66 shifts Gn(r)|Z=Z1 in the r direction according to the shift amount of the peak position r1 and the peak position r2. Specifically, the estimation unit 66 shifts the deconvolution operation data Gn(r)|Z=Z1 in the r direction by (r2−r1)×Z1/(Z2−Z1) to calculate the estimation data Gn(r)|Z=Z0. Specifically, the estimation unit 66 obtains the estimation data of the deconvolution operation data based on the following Expression (2).

$$Gn(r)|_{Z=Z0} = Gn(r + (r2 - r1) \times Z1 / (Z2 - Z1))|_{Z=Z1} \qquad (2)$$

As described above, the estimation unit 66 calculates the estimation data Gn(r)|Z=Z0 of the deconvolution operation data in the focusing position (Z=Z0) by shifting the deconvolution operation data Gn(r)|Z=Z1 in the non-focal position (Z=Z1). As a matter of course, the estimation unit 66 may calculate the estimation data Gn(r)|Z=Z0 by shifting the deconvolution operation data Gn(r)|Z=Z2. As shown in FIG. 6, the estimation data of the deconvolution operation data in Z=Z0 is also extended in the region where r is negative. As shown in FIG. 6, the peak position r0 of Gn(r)|Z=Z0 is at a position close to r=0.

The estimation unit 66 estimates the estimation data Gn(r)|Z=Z0 for each circumferential position. The synthesis unit 67 synthesizes the estimation data Gn(r)|Z=Z0 that is estimated for each circumferential position to generate the deconvoluted image in the focusing position (Z=Z0). That is, the processing apparatus 16 calculates the estimation data for all the θ components. The synthesis unit 67 sums up all the θ components obtained for each angle component to reproduce the deconvoluted image. The deconvoluted image G(r,θ) can be calculated based on the following Expression (3).

$$G(r, \theta) = \sum_{\theta} G_n(r) \qquad (3)$$

Figure 7:
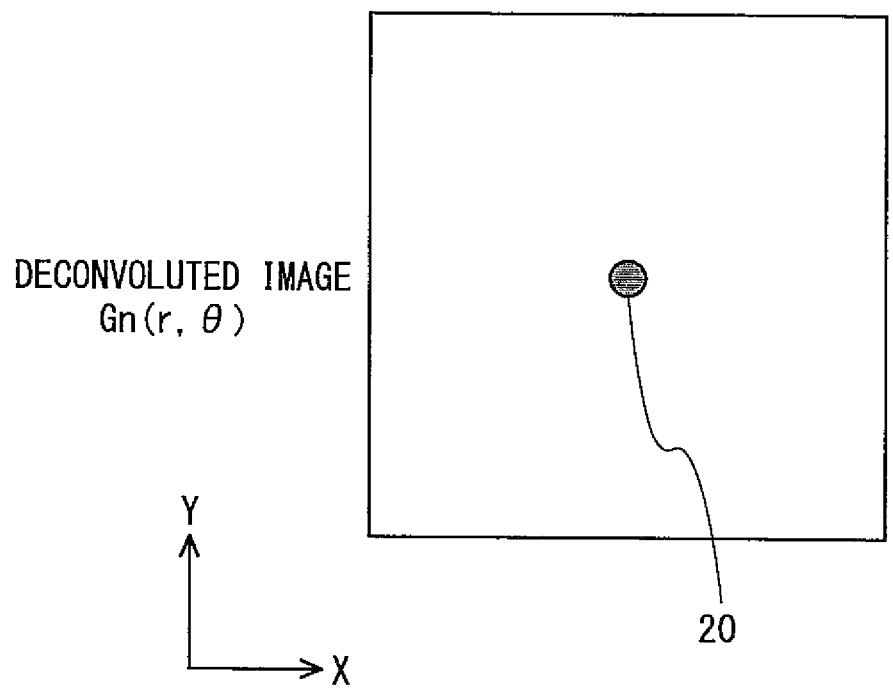
FIG. 7 is a diagram showing a deconvoluted image in the focusing position.

The processing apparatus 16 converts the deconvoluted image Gn(r,θ) into the XY rectangular coordinate system to display the XY rectangular coordinate system on a monitor or the like. FIG. 7 shows the deconvoluted image in the focusing position calculated by the above processing. As stated above, the processing apparatus 16 extracts the characteristics of the deconvolution operation data in different focal positions in the optical axis direction. The processing apparatus 16 then estimates the estimation data of the deconvolution operation data in a desired focal position in the optical axis direction by the linear interpolation or the like. When Z=Z0, which is a focusing position, is obtained, the processing apparatus 16 is able to obtain the estimation data in the focusing position. The processing apparatus 16 sums up the estimation data obtained for each angle component to calculate the deconvoluted image.

By carrying out the deconvolution operation using the one-dimensional point spread function, it is possible to reduce the blurring of the image due to wavefront aberration. When the concave mirror 15a with the hole is large in size, for example, it is difficult to polish the reflection surface with high accuracy. In such a case, due to wavefront aberration, scattered light beams scattered from one observation point are not focused on one position on the light receiving surface of the TDI camera 19. For example, the scattered light scattered at a specific scattering angle is made incident on a position different from a position on which a scattered light scattered at another scattering angle is made incident. Therefore, the optical image is blurred when the scattered light intensity distribution varies for each scattering angle.

As described above, even when the intensity distribution for each scattering angle is different depending on the target to be observed, it is possible to accurately reproduce the real image by the above processing. Further, in this embodiment, the deconvolution operation using the one-dimensional point spread function has been performed on the profile data in the r direction. According to this deconvolution operation, even when the scattered light intensity distribution is different for each scattering angle, it is possible to obtain an accurate image. Meanwhile, in the deconvolution operation using the two-dimensional point spread function, when the scattering angle intensity is different for each scattering angle direction, it is difficult to correct the blurring of the image due to an aberration. On the other hand, since in this embodiment the deconvolution operation using the one-dimensional point spread function is used, the processing can be simplified.

Further, in this embodiment, the deconvoluted image in the focusing position is calculated using the images in the non-focal positions. According to this operation, it is possible to calculate an appropriate deconvoluted image.

While the focused image is synthesized based on two images in the above embodiments for the sake of simplification of the description, the focused image may be synthesized based on three or more images. That is, three or more pieces of profile data may be used to estimate the estimation data of the deconvolution operation data in the focusing position. When three or more pieces of profile data are used, for example, the processing apparatus 16 calculates peak positions r1-r3 corresponding to the profile data. It is then possible to obtain the peak position r0 of the focusing position according to the least-squares method using the peak positions r1-r3. In this case, it is possible to more accurately estimate the peak position of the deconvolution operation data in the focusing position.

The point spread function PSFn(r) can be obtained from the captured image when the actual point image is captured. Otherwise, it is possible to obtain the point spread function PSFn(r) by a simulation or the like according to a measured value of the shape of the reflection surface of the convex mirror 15b or the concave mirror 15a with the hole.

Second Embodiment

In this embodiment, processing in the profile data generation unit 64, the deconvolution operation unit 65, and the estimation unit 66 in the first embodiment is modified. Since the configurations other than the processing in the profile data generation unit 64, the deconvolution operation unit 65, and the estimation unit 66 are similar to those in the first embodiment, the description thereof will be omitted. For example, the configuration of the inspection apparatus 100 and the configurations of the processing in the first storage unit 61, the second storage unit 62, and the synthesis unit 67 and the like are similar to those in the first embodiment.

Figure 8:
FIG. 8 is a diagram for describing profile data.

In the profile data Fn(r), the direction in which r is developed according to the increase in the Z coordinate may be different depending on whether the scattering direction of the scattered light is positive or negative. It is assumed, for example, as shown in FIG. 8, in the focusing position, there is a profile having a peak at around r=0. It is also assumed that the scattered light includes a component that shifts in the positive direction of r and a component that shifts in the negative direction of r according to the increase in Z. In this case, as shown in FIG. 8, two peaks appear separately from each other by changing the Z position. The peak due to the component that is developed in the positive direction of r according to the increase in Z is denoted by $P^+$ and the peak due to the component that is developed in the negative direction of r is denoted by $P^-$.

When Z is increased from Z1 to Z2, as shown in FIG. 8, the peak $P^+$ is shifted in the positive direction and the peak $P^-$ is shifted in the negative direction. Accordingly, the image is split with the increase in the Z position. As described above, when the shift amount of the peak is obtained by the method in the first embodiment when there are positive and negative development components, the estimation accuracy may be degraded. In order to solve this problem, in this embodiment, the shift amount of the peak is obtained based on a main component. In this example, the positive peak $P^+$ is larger than the negative peak $P^-$, which means the positive peak $P^+$ is regarded as being the main component. The processing apparatus 16 therefore obtains the shift amount based on the peak position of the positive peak $P^+$.

The processing apparatus 16 extracts the characteristics of two waveforms of the profile data Fn(r)|Z=Z1 and the profile data Fn(r)|Z=Z2 to obtain the shift amount of the main component in the r direction. Therefore, the profile data generation unit 64 introduces an offset variable a in the r direction of Fn(r)|Z=Z2. The profile data generation unit 64 carries out the integration in the r direction of the convolution of Fn(r)|Z=Z1 and Fn(r−a)|Z=Z2. When data calculated by the integration in the r direction of convolution is denoted by Hn(a), the profile data generation unit 64 carries out the convolutional integration by the following expression (4) to obtain Hn(a).

$$Hn(a)=\int F_n(r)|_{Z=Z1} \times F_n(r-a)|_{Z=Z2} dr \quad (4)$$

As described above, the profile data generation unit 64 performs the convolution operation on two pieces of profile data at different Z positions to generate the convolution operation data Hn(a). The profile data generation unit 64 obtains the value where Hn(a) becomes the maximum as the offset value a. The offset value a is a value indicating the shift amount of the peak position of the positive peak $P^+$, which is the main component. That is, the difference between the peak position of the peak $P^+$ when Z=Z1 and the peak position of the peak $P^+$ when Z=Z2 is the offset value a.

Figure 9:
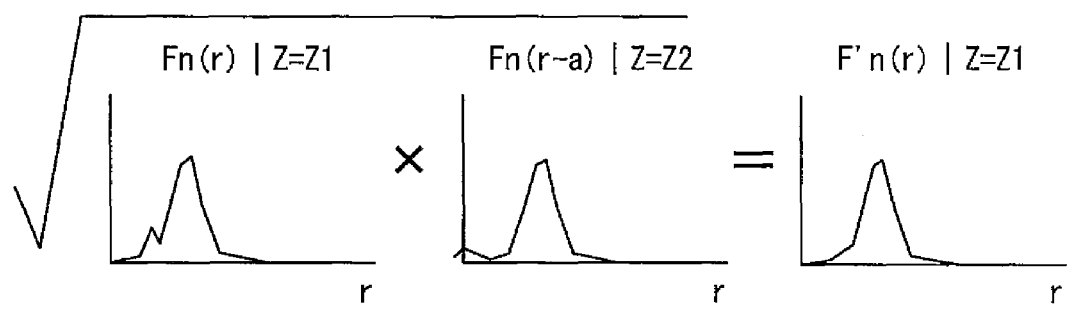
FIG. 9 is a diagram for describing processing for estimating deconvolution data in the focusing position using the deconvolution operation data.

As shown in FIG. 9, the profile data generation unit 64 obtains the offset value a and then the square root of the product of Fn(r)|Z=Z1 and Fn(r−a)|Z=Z2. Then, as shown in Expression (5), the profile data generation unit 64 replaces the square root of the product thereof by the profile data F'n(r)|Z=Z1. F'n(r) is a positive value.

$$F'n(r)|_{Z=Z1} = (Fn(r)|_{Z=Z1} \times Fn(r-a)|_{Z=Z2})^{1/2} \quad (5)$$

The profile data generation unit 64 obtains the square root of the product of Fn(r)|Z=Z1 and Fn(r-a)|Z=Z2 as the profile data F'n(r). According to this operation, it is possible to cancel the components having a sign different from that of the main component in the r direction of the scatter component. That is, since the shift amount of the negative peak $P^-$ of Z=Z1, Z2 is different from the shift amount of the positive peak $P^+$, the negative peak $P^-$ becomes small in F'n(r). From the above description, by using a value of the product of Fn(r)|Z=Z1 and Fn(r-a)|Z=Z2 to the power of ½, the peaks other than the main component can be reduced.

The deconvolution operation unit 65 executes the deconvolution operation on the profile data F'n(r) using the one-dimensional point spread function. It is therefore possible to obtain the deconvolution operation data Gn(r)|Z=Z1. Then, the estimation unit 66 shifts Gn(r)|Z=Z1 in the r direction by the shift amount of the peak position, whereby the estimation data Gn(r)|Z=Z0 can be calculated. The calculation of the estimation data Gn(r)|Z=Z0 may be performed, for example, using the following Expression (6).

$$Gn(r)|_{Z=Z0} = Gn(r + a \times Z1/(Z2 - Z1))|_{Z=Z1} \quad (6)$$

Figure 10:
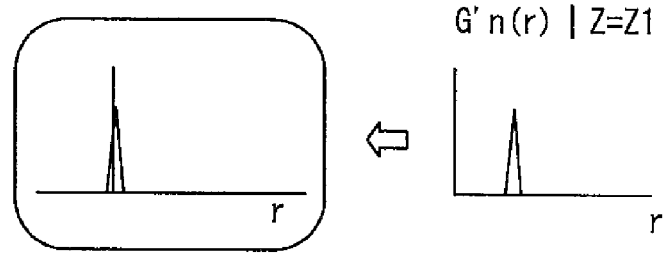
FIG. 10 is a diagram showing estimation data in the focusing position obtained using the deconvolution operation data.

FIG. 10 shows the deconvolution data obtained by Expression (6). By carrying out the above processing, the accuracy of the deconvoluted image can be improved. Even when the light scattering component in the positive direction is different from that in the negative direction, only the main component can be obtained. It is therefore possible to improve the accuracy of the deconvoluted image and to generate an optical image in which blurring due to wavefront aberration is suppressed. In this embodiment as well, the deconvolution operation unit 65 carries out the deconvolution operation using the one-dimensional point spread function to generate the deconvolution operation data based on the profile data. Accordingly, it is possible to suppress the blurring due to the wavefront aberration, similar to the first embodiment.

While two images, the first image and the second image, have been used in the above embodiments, three or more images may be used. Further, the method for calculating the peak positions or the shift amount of the peak position is not limited to the above processing and various other methods may be used.

Further, while the estimation data in the focusing position has been calculated based on the profile data in the non-focal positions in the first and second embodiments, the estimation data in the non-focal position may be calculated instead of calculating the estimation data in the focusing position. That is, the processing apparatus 16 may estimate the estimation data in a desired focal position in the optical axis direction based on a plurality of images captured in different focus positions in the optical axis direction. The processing apparatus 16 may synthesize, based on the estimation data in the desired focal position, the image in the desired focal position. As described above, it is possible to capture a plurality of images in positions other than a given Z position and to obtain the deconvoluted image in the given Z position.

Third Embodiment

In this embodiment, a mask inspection apparatus, which is one example of an application of a coordinate detection apparatus that detects coordinates of a pattern, will be described. For example, a pattern such as a fiducial mark is formed in the mask, which is a sample. The coordinate detection apparatus arranged in the mask inspection apparatus detects the coordinates of the pattern. Since a configuration of an inspection apparatus is similar to that of the first embodiment as illustrated in FIG. 1, the description thereof will be omitted. In the third embodiment, the process executed by the processing unit 16 as illustrated in FIG. 1 is different from that of the first embodiment. Specifically, the processing unit 16 has a coordinate detection apparatus. The coordinate detection method according to this embodiment will be described.

The processing apparatus 16 carries out image processing on the image of the mask 14 to detect a fiducial mark formed in the mask 14. The processing apparatus 16 stores the coordinates of the fiducial mark as reference coordinates. The processing apparatus 16 determines the coordinates of the defect based on the reference coordinates. The defect is then detected based on the image captured by the TDI camera 19. Since a known method can be used when the defect is detected, the description thereof will be omitted.

Further, the mask 14 includes a fiducial mark (alignment mark) for performing an alignment. The coordinates of the defect are detected using the coordinates (XY positions) of the fiducial mark as the reference coordinates. For example, the fiducial mark is detected by the TDI camera 19 to use the coordinates of the fiducial mark as the reference coordinates. After the stage 13 is moved to a predetermined position, the TDI camera 19 captures the image of the mask 14. The processing apparatus 16 then detects the defect based on the image captured by the TDI camera 19. The coordinates (XY positions) of the defect in the mask 14 are detected based on the position (pixel coordinates) of the defect in the captured image, the coordinates of the fiducial mark, and the driving amount of the stage 13.

Figure 11:
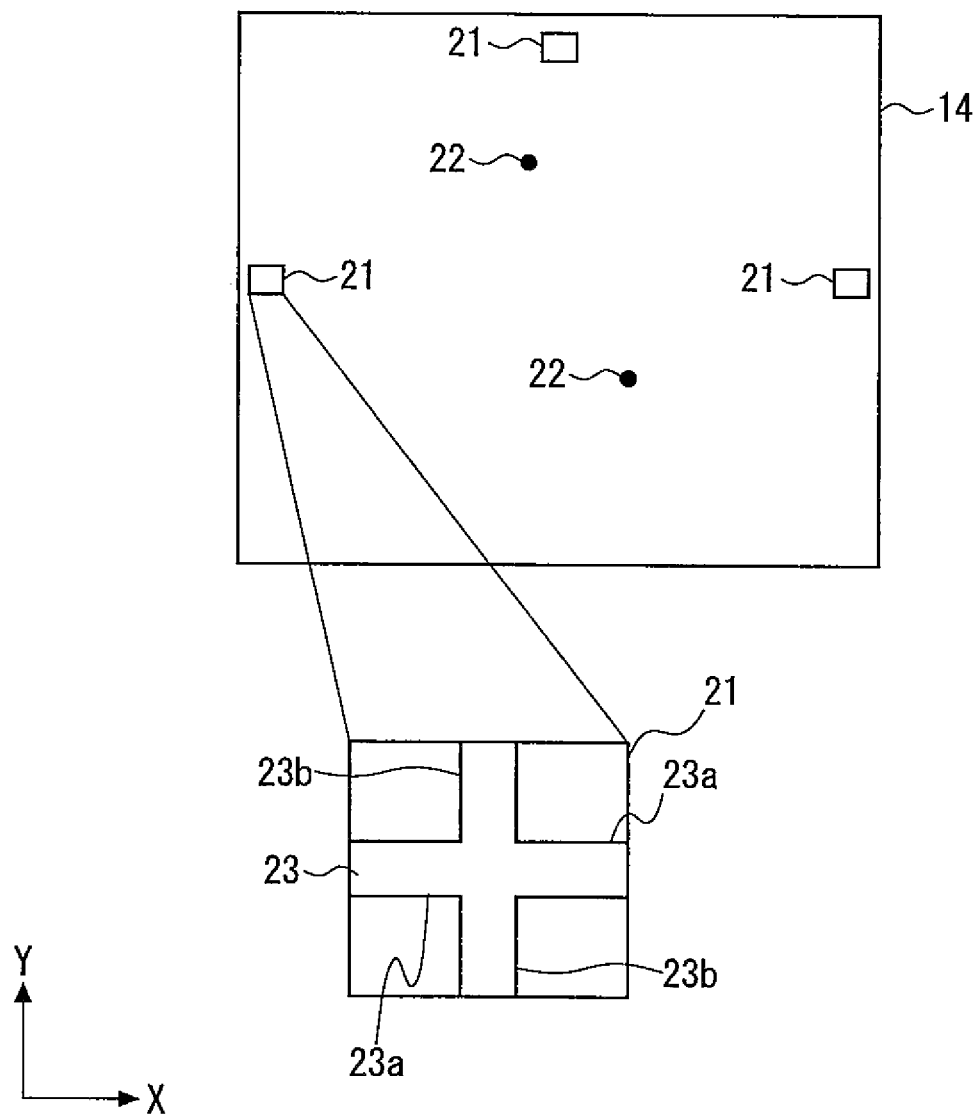
FIG. 11 is a plane view schematically showing a fiducial mark provided in a mask.

Next, with reference to FIG. 11, the fiducial mark 23 and a fiducial area 21 formed in the mask 14 will be described. FIG. 11 is an XY plane view showing the fiducial area 21 formed in the mask 14. Further, FIG. 11 shows in the lower part an enlarged view of the fiducial area 21.

When the mask 14 has a size of 152 mm square, for example, an area in which a pattern is transferred has a size of about 100 mm to 120 mm square and the fiducial area 21 has a size of about 50 μm square. As a matter of course, the number of the fiducial areas 21 and the size and the arrangement thereof are not particularly limited. In FIG. 11, two defects 22 are attached to an exposed area.

The fiducial mark 23 is formed in the fiducial area 21. The fiducial mark 23 is formed of a cross pattern in the form of crossing lines on the XY plane view. The fiducial mark 23 includes two edges 23a along the X direction and two edges 23b along the Y direction. The processing apparatus 16 detects the coordinates of the defect 22 based on the fiducial mark 23. That is, since the processing apparatus 16 detects the coordinates of the fiducial mark 23, the coordinates of the defect are obtained from the driving amount (moving distance) or the like of the stage 13 from the detected coordinates of the fiducial mark 23.

When the defect mitigation is carried out, in the step of drawing a pattern, a pattern of an absorber is formed in the mask 14 to prevent the defect 22 from being transferred into a semiconductor wafer. For example, the pattern of the absorber is formed in such a way that all the defects 22 in the exposed area are immediately below the pattern of the absorber. When an exposure is carried out using the mask 14 having the defect 22 immediately below the pattern of the absorber, the defect 22 is not transferred into the semiconductor wafer. That is, even when the defect 22 is present immediately below the absorber, pattern abnormalities do not occur since the absorber absorbs light. It is therefore possible to improve the productivity of semiconductors.

Figure 12:
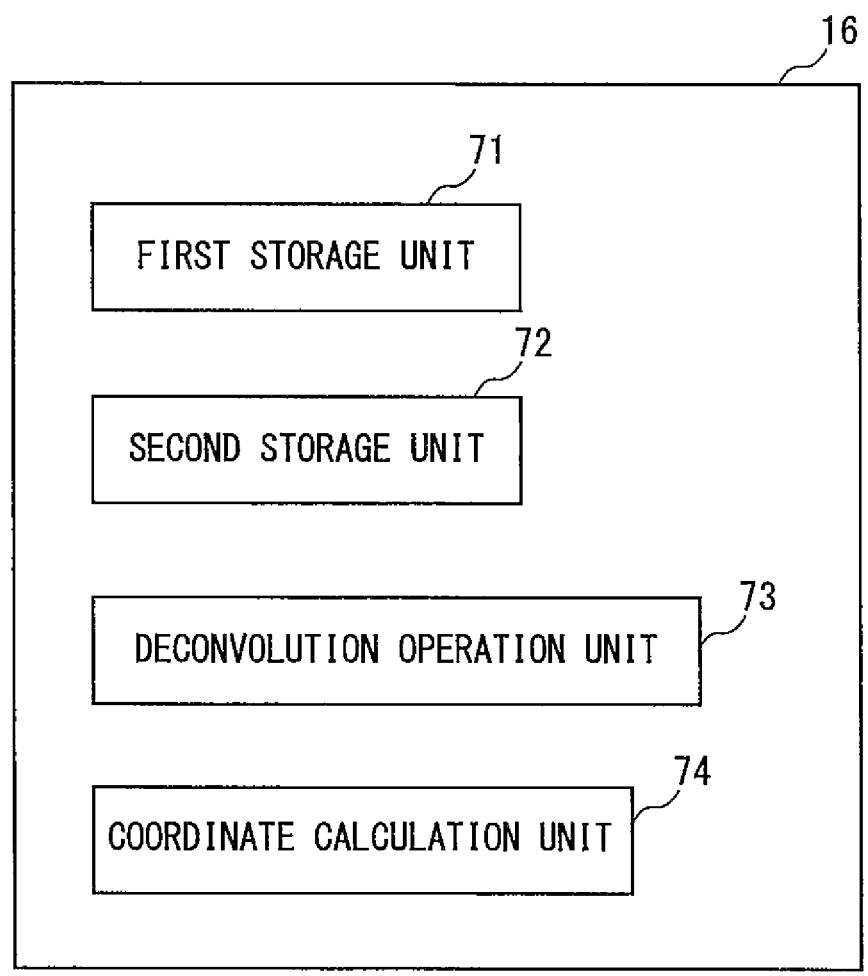
FIG. 12 is a block diagram showing a configuration of a processing apparatus used in an inspection apparatus according to a third embodiment.

Next, a method for detecting the coordinates of the fiducial mark 23 will be described. FIG. 12 is a block diagram showing a configuration of the processing apparatus 16. The processing apparatus 16 includes a first storage unit 71, a second storage unit 72, a deconvolution operation unit 73, and a coordinate calculation unit 74.

The first storage unit 71 stores the image of the mask captured by the TDI camera 19. The captured image includes the fiducial mark 23 of the mask 14. When the inspection is completed, for example, the stage 13 is driven and is moved to the fiducial area 21 of the mask 14. The first storage unit 71 then stores the image captured by the TDI camera 19 (hereinafter referred to as a captured image). In the captured image, the XY coordinates (XY positions) and luminance data are associated with each other. The XY coordinates may be pixel coordinates in the TDI camera 19 or may be real coordinates according to the size of one pixel of the TDI camera 19.

The second storage unit 72 stores the reference image used in the deconvolution operation. In the reference image, the XY coordinates (XY positions) and the luminance data are associated with each other. The XY coordinates may be pixel coordinates in the TDI camera 19 or may be an actual dimension according to the size of one pixel of the TDI camera 19. The reference image has a size the same as that of the captured image. The reference image and the captured image are, for example, two-dimensional images having 1024 pixels×1024 pixels.

The reference image may be an image including the fiducial mark 23. In this embodiment, the second storage unit 72 stores, as the reference image, an image including the fiducial mark 23 whose XY coordinates are known. For example, an image including the fiducial mark 23 at the center thereof is used as the reference image. The reference image is an image acquired by the TDI camera 19 of the inspection apparatus 100. For example, the XY coordinates of the fiducial mark 23 in the image are obtained by a method such as an edge detection, thereby obtaining the reference image.

The deconvolution operation unit 73 carries out the deconvolution operation using the reference image and the captured image to generate the deconvolution operation data. The coordinate calculation unit 74 detects the coordinates of the fiducial mark 23 based on the deconvolution operation data.

In the following description, the reason why the coordinates of the fiducial mark can be detected by the deconvolution operation processing will be described. When a function indicating the shape of the object is denoted by f and an arbitrary convolution function by g, a convolution integral $(f*g)(t)$ can be expressed by the following Expression (7).

$$(f*g)(t) = \int f(u) \cdot g(t-u) du \quad (7)$$

In Expression (7), u denotes a variable that indicates the position of the reference image. In the following description, for the sake of clarification of the description, a case in which a one-dimensional deconvolution operation is performed will be described. The symbols f(u) and g(u) denote luminance data in the position u. When the function g is a function obtained by offsetting the delta function δ by a, the following expression (8) is obtained.

$$(f*g)(t) = \int f(u) \cdot g(t-u) du = \int f(u) \cdot \delta(t-a-u) du \quad (8)$$

When u=t−a, δ(t−a−u)=1 is satisfied. Therefore, when u=t−a, (f*g)(t)=f(t−a) is satisfied. That is, when the function defined by g(t)=δ(t−a) is convolved with f(t), the object image of f(t−a), which is offset by a, is obtained.

From the above relation, when the reference image is defined to be f(t) and the image obtained by offsetting the position of the reference image by a is defined to be (f*g)(t), which is the result of the convolution integral, the result of deconvolving (f*g)(t) with f(t) can be expressed by δ(t−a). That is, by obtaining the value a of t where the deconvoluted image becomes 1, the offset amount of the image can be estimated.

By applying these principles, it is possible to obtain the shift amount of the position with respect to the image having an arbitrary shape. Assume, for example, that the reference image is (f*g)(t) and the captured image is f(t). By carrying out the deconvolution operation using the reference image and the captured image, the deconvoluted image g(t) can be obtained. Then, the value of a where luminance data of the deconvoluted image g(t)=δ(t−a) is 1 is calculated as the offset amount of the image.

Figure 13:
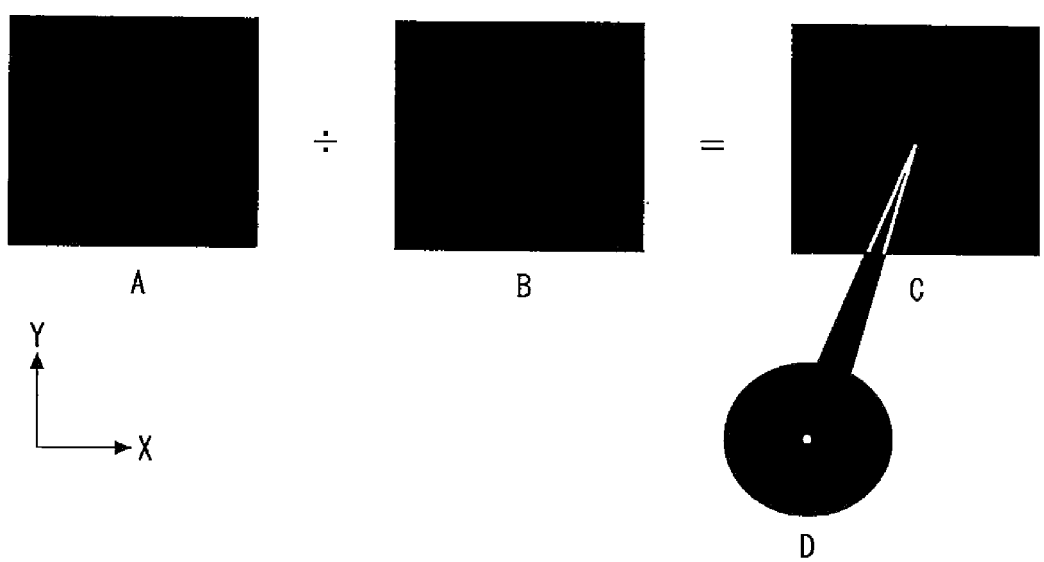
FIG. 13 is a diagram showing data before a deconvolution operation in a processing method according to the third embodiment.

As described above, when the captured image and the reference image are completely coincident with each other, the δ function having the center of 1 is the deconvoluted image. With reference to FIG. 13, a case in which the captured image and the reference image are completely coincident with each other will be described. In FIG. 13, an image A shows the reference image, an image B shows the captured image, and an image C shows the deconvoluted image. Further, in the image C in FIG. 13, the central position of the deconvoluted image is shown in an enlarged manner (an image D). In FIG. 13, each of the images A to C is formed of 1024 pixels (X)×1024 pixels (Y).

In the reference image A, the cross-shaped fiducial mark is located at the center of the XY direction. Further, the captured image B is coincident with the reference image A. Therefore, in the captured image B also, the cross-shaped fiducial mark is located at the center of the XY direction. By carrying out the deconvolution operation on the reference image A using the captured image B, the deconvoluted image C can be obtained. There is a bright spot at the center of the deconvoluted image C. That is, ideally, the deconvoluted image is an image in which the luminance data at the center (512, 512) of the deconvoluted image C is 1.0 and the luminance data in the other parts is 0.

For example, an image in which the point spread function is convoluted into the reference image A is the captured image B. Accordingly, when the reference image A and the captured image B are coincident with each other, the point spread function is the δ function δ(t) having the center of 1. That is, in FIG. 13, the point spread function is the δ function in which the luminance data at the center of the deconvoluted image C is 1 and the luminance data in the other parts is 0.

On the other hand, when the captured image B is deviated from the reference image A by a, the δ function δ(t−a), where the position in which the deconvoluted image C becomes 1 is offset by a, is obtained. Therefore, the deviation amount can be obtained by obtaining a. That is, when the captured image B is deviated from the reference image A by a, the point spread function is the δ function in which the luminance data at a is 1 and the luminance data in the other parts is 0.

Figure 14:
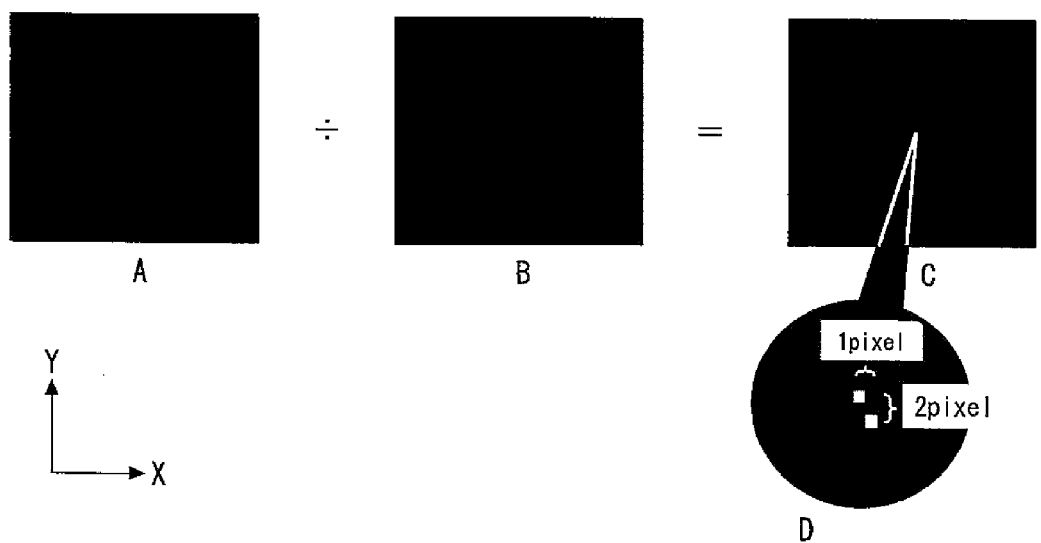
FIG. 14 is a diagram showing data after the deconvolution operation in the processing method according to the third embodiment.

With reference to FIG. 14, a case in which the captured image B is shifted from the reference image A will be described. In FIG. 14, the captured image B is deviated from the reference image A by 1.5 pixels in the X direction (right) and 2.5 pixels in the Y direction (down). That is, in the captured image B, the cross-shaped fiducial mark is shifted in a right-downward direction. In FIG. 14, the image A shows the reference image, the image B shows the captured image, and the image C shows the deconvoluted image. Further, in the image C in FIG. 14, the central position of the deconvoluted image is enlarged (an image D). In FIG. 14, each of the images A to C is formed of 1024 pixels (X)×1024 pixels (Y).

In the reference image A, the cross-shaped fiducial mark is located at the center of the XY direction. By carrying out the deconvolution operation on the reference image A using the captured image B, the deconvoluted image C is obtained. In the deconvoluted image C, the bright spot is shifted in a right-downward direction from the center of the image. For example, in the deconvoluted image C, the bright spot is deviated by one pixel to the right and two pixels down. In this example, the shift amount of the bright spot corresponds to the shift amount of the captured image B with respect to the reference image A. Accordingly, the shift amount can be obtained by obtaining the coordinates of the bright spot based on the deconvolution operation data. For example, the central coordinates of the bright spot correspond to the shift amount between the captured image and the reference image. By obtaining the shift amount, it is possible to accurately detect the coordinates of the fiducial mark 23 in the captured image.

Specifically, the deconvolution operation unit 73 carries out the deconvolution operation using the reference image A and the captured image B. Therefore, the deconvolution data can be obtained. The deconvolution data forms the deconvoluted image C in which the XY positions and the luminance data are associated with each other.

The coordinate calculation unit 74 obtains the shift amount from the deconvolution operation data. Specifically, the position of the center of mass of the deconvoluted image C is obtained. The coordinate calculation unit 74 then sets the difference between the central position and the position of the center of mass of the deconvoluted image C as the shift amount. That is, by subtracting the central coordinates of the image from the coordinates of the center of mass of the deconvoluted image C, the shift amount can be obtained. According to this operation, it is possible to easily calculate the shift amount of the captured image with respect to the reference image. Since the XY coordinates of the fiducial mark 23 in the reference image are already known, the coordinates of the fiducial mark 23 in the captured image may be accurately detected.

As described above, the deconvolution operation unit 73 carries out the deconvolution operation to generate the deconvolution operation data. The coordinate calculation unit 74 detects the coordinates of the fiducial mark 23 based on the shift amount between the reference image A and the captured image C. It is therefore possible to accurately detect the fiducial mark 23 with high repeatability. Further, since the coordinates can be accurately detected, it is possible to carry out the alignment with high accuracy. Still further, since there is no need to detect the edges of the fiducial mark 23, the coordinates can be detected by simple processing.

Further, the image including the fiducial mark 23 captured using a measuring optical system of the inspection apparatus 100 is used as the reference image A. It is therefore possible to carry out image processing on the fiducial mark 23 having an arbitrary shape. For example, while the image processing algorithm needs to be re-considered according to the type of the fiducial mark in the coordinate detection method according to the related art, it is possible to detect the coordinates of the fiducial mark having an arbitrary shape in the above image processing method.

Further, the shift amount is calculated based on the position of the center of mass of the deconvoluted image. It is therefore possible to calculate the shift amount for each sub-pixel. Further, by analyzing the extension of the bright spot or the like, information other than the position shift (e.g., noise, blurring, and rotation components of the image) may be obtained through digitalization.

While the fiducial mark 23 is located at the center of the reference image A in the above description, the position of the fiducial mark 23 is not limited to the center of the reference image A. When the position of the fiducial mark 23 in the reference image A is known, it is possible to accurately detect the coordinates of the fiducial mark 23 from the shift amount between the reference image A and the captured image B. Then the coordinates of the fiducial mark 23 in the captured image B may be converted into the coordinates of the stage 13. According to this operation, an accurate alignment can be achieved and the accuracy of detecting the coordinates of the defect can be improved. It is therefore possible to cover the defect with the pattern of the absorber without failure when the defect mitigation is carried out.

While the shift amount of the captured image B with respect to the reference image A has been obtained in the above description, the shift amount of the reference image A with respect to the captured image B may be obtained. In this case, the coordinates of the bright spot are shifted in the deconvoluted image C in the direction opposite to the direction in which they are shifted when the shift amount of the captured image B with respect to the reference image A is obtained. Even in such a case, it is possible to accurately detect the coordinates.

Fourth Embodiment

When an image is blurred, it may not be possible to accurately detect the coordinates of the fiducial mark. It is observed, when the edge of the fiducial mark is regarded as being a linear light source, that the image of the edge of the fiducial mark that is captured is linearly distorted. When the image captured in the focus position deviated from the focal position is acquired, the fiducial mark is blurred. In order to deal with this problem, in this embodiment, it is assumed that the distortion of the edge of the captured image of the fiducial mark occurs due to the line spread function LSF and the deconvolution operation by the line spread function is carried out. That is, the edge is regarded as a linear light source and the deconvolution operation is carried out using the line spread function.

In this embodiment, processing in the processing apparatus 16 is different from that in the third embodiment. Since the basic configuration and the processing other than the processing in the processing apparatus 16 are similar to those in the first to third embodiments, the description thereof will be omitted. For example, the configuration of the inspection apparatus 100 is similar to that in the first embodiment.

Figure 15:
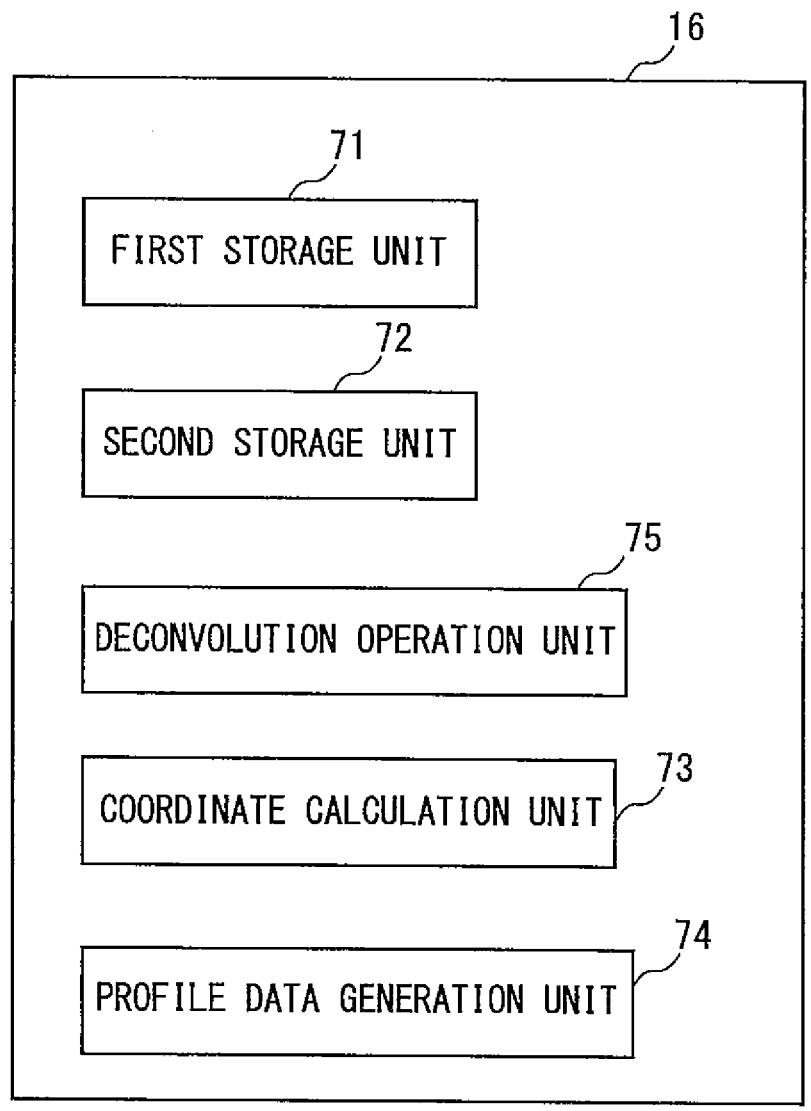
FIG. 15 is a block diagram showing a configuration of the processing apparatus used in the inspection apparatus according to the fourth embodiment.

FIG. 15 shows a configuration of the processing apparatus 16 according to this embodiment. FIG. 15 shows, besides the configuration of FIG. 12, a profile data generation unit 75. Similar to the third embodiment, the first storage unit 71 stores the captured image.

The second storage unit 72 stores the line spread function that has been prepared in advance. The line spread function LSF is data in which characteristics of edges captured through the measuring optical system of the inspection apparatus 100 are expressed. The line spread function is one-dimensional data and is obtained for each of the line image in the X direction and the line image in the Y direction. For example, in the line spread function LSF of the line along the X direction (edges 23a), the Y coordinates and the luminance data are associated with each other. In the line spread function LSF of the line along the Y direction (edges 23b), the X coordinates and the luminance data are associated with each other. Therefore, the line spread function of the line along the X direction is expressed by LSF(y) and the line spread function of the line along the Y direction is expressed by LSF(x). For example, the line spread function can be generated based on the image obtained by capturing the linear light source in the inspection apparatus 100.

The profile data generation unit 75 generates the profile data in the X direction and the profile data in the Y direction based on the captured image. The profile data in the X direction is data in which the position in the X direction and the luminance data are associated with each other. The profile data in the Y direction is data in which the position in the Y direction and the luminance data are associated with each other. Further, the profile data generation unit 75 extracts the profile data in the X direction for each of the positions in the Y direction. That is, different profile data are generated in different positions in the Y direction. Therefore, the profile data generation unit 75 generates a plurality of pieces of profile data in the X direction. Specifically, the profile data generation unit 75 generates profile data $[P_{Y1}(x), P_{Y2}(x), P_{Y3}(x) \ldots]$ for the Y direction positions [Y1, Y2, Y3, ...], respectively.

In a similar way, the profile data generation unit 75 extracts the profile data in the Y direction for each position of the X direction. Therefore, the profile data generation unit 75 generates a plurality of pieces of profile data in the Y direction. Specifically, the profile data generation unit 75 generates profile data $[P_{X1}(y), P_{X2}(y), P_{X3}(y) \ldots]$ for the X direction positions [X1, X2, X3, ...], respectively.

The deconvolution operation unit 73 carries out the deconvolution operation using the line spread function and the profile data. According to this operation, the deconvolution operation data is generated. The deconvolution operation unit 73 carries out the deconvolution operation using the profile data in the X direction P(x) and the line spread function LSF(x) of the line along the Y direction. In a similar way, the deconvolution operation unit 73 carries out the deconvolution operation using the profile data in the Y direction P(y) and the line spread function LSF(y) of the line along the X direction.

Figure 16:
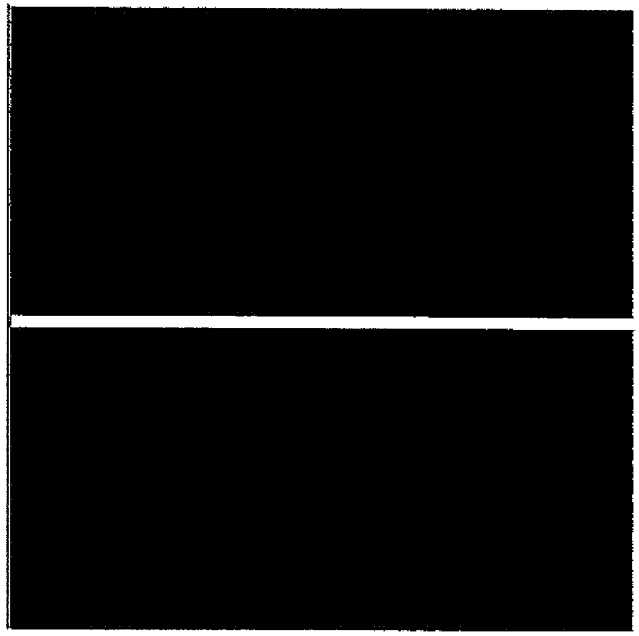
FIG. 16 is a diagram showing data before the deconvolution operation in the processing method according to the fourth embodiment.
Figure 17:
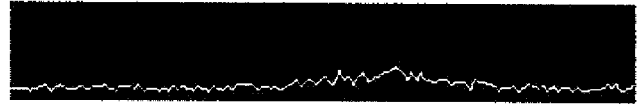
FIG. 17 is a diagram showing data before the deconvolution operation in the processing method according to the fourth embodiment.
Figure 18:
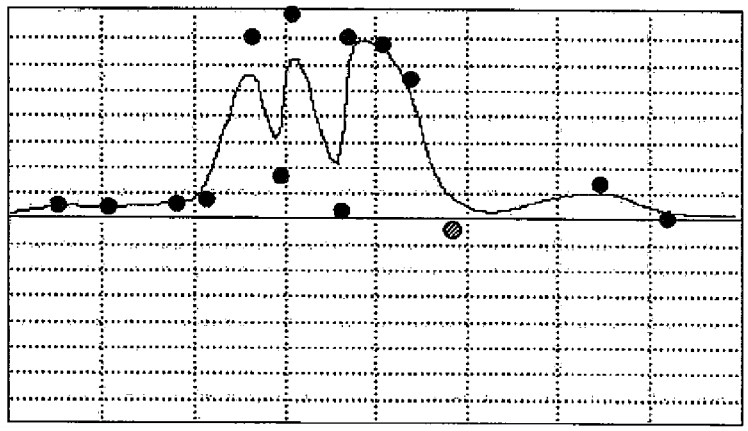
FIG. 18 is a diagram showing data before the deconvolution operation in the processing method according to the fourth embodiment.
Figure 19:
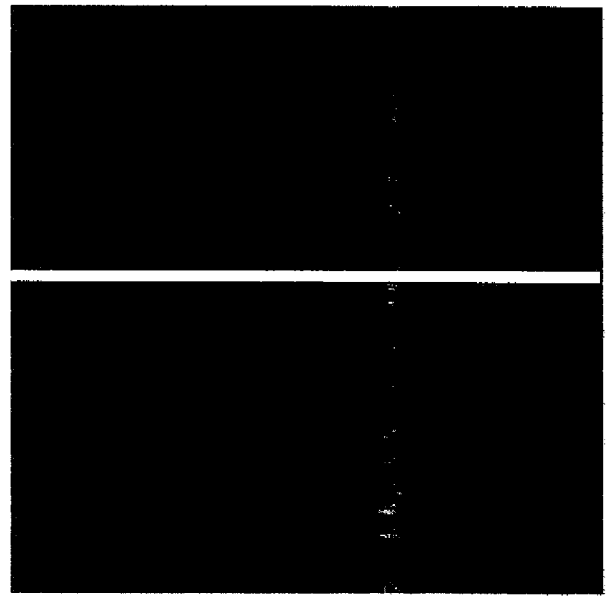
FIG. 19 is a diagram showing data after the deconvolution operation in the processing method according to the fourth embodiment.
Figure 20:
FIG. 20 is a diagram showing data after the deconvolution operation in the processing method according to the fourth embodiment.
Figure 21:
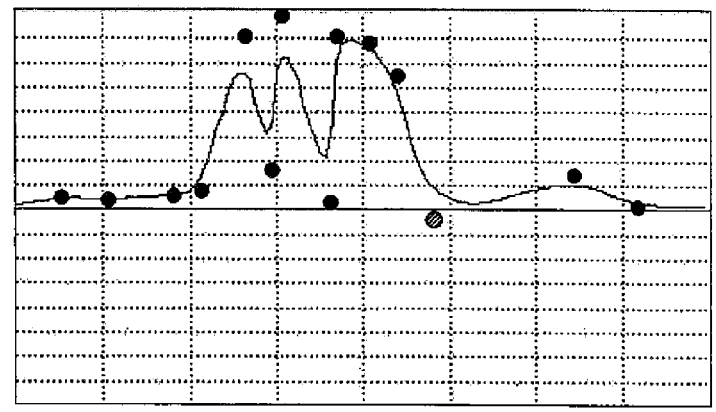
FIG. 21 is a diagram showing data after the deconvolution operation in the processing method according to the fourth embodiment.

With reference to FIGS. 16 and 21, the deconvolution operation processing will be described. FIGS. 16 to 18 are diagrams showing data before the deconvolution operation. Specifically, FIG. 16 shows a two-dimensional captured image, FIG. 17 shows the profile data in the X direction, and FIG. 18 shows the line spread function LSF(x) of the line along the Y direction. FIGS. 19 to 21 are diagrams showing the deconvolution operation data which has been subjected to the deconvolution operation processing using the line spread function LSF. FIG. 19 shows a two-dimensional deconvoluted image, FIG. 20 shows the profile data in the X direction which has been subjected to the deconvolution operation (one-dimensional deconvolution data), and FIG. 21 shows the line spread function LSF(x). In FIG. 16 and FIG. 19, the edges along the vertical direction (Y direction) of the fiducial mark are enlarged.

In the image data before carrying out the deconvolution operation, as shown in FIG. 16, the captured image is blurred. Therefore, as shown in FIG. 17, the peak of the edges is lowered in the profile data in the X direction P(x). When the deconvolution operation is not carried out, it is difficult to accurately detect the position of the edge of the fiducial mark.

When the deconvolution operation is carried out, as shown in FIG. 19, the blurring of the image is reduced. Therefore, as shown in FIG. 20, the peak of the edges becomes high as in the one-dimensional deconvolution profile data. It is therefore difficult to accurately detect the position of the edges of the fiducial mark.

The deconvolution operation unit 73 carries out the deconvolution operation on each of the plurality of pieces of profile data in the X direction $[P_{Y1}(x), P_{Y2}(x), P_{Y3}(x) \ldots]$. The deconvolution operation is carried out on the profile data in the X direction $[P_{Y1}(x), P_{Y2}(x), P_{Y3}(x) \ldots]$ using a common line spread function LSF(x).

Each of the deconvolution operation data is one-dimensional data. The coordinate calculation unit 74 synthesizes the plurality of pieces of one-dimensional deconvolution operation data, whereby a two-dimensional deconvoluted image is formed. By detecting the edges of the fiducial mark, the coordinate calculation unit 74 detects the X coordinate of the fiducial mark in the image.

The coordinate calculation unit 74 obtains, for example, the central position of the edges of the cross-shaped fiducial mark in each of the Y coordinates (Y1, Y2, Y3 ...) as the edge coordinates. Then the midpoint of the edge coordinates of the right and left two edges 23b is set to be the X coordinates $(E_{Y1}, E_{Y2}, E_{Y3} \ldots)$ of the fiducial mark in each Y coordinate. The average value of the X coordinates $(E_{Y1}, E_{Y2}, E_{Y3} \ldots)$ of the fiducial mark in the plurality of X coordinates is set to be the X coordinate of the fiducial mark. In this way, the X direction position (X coordinate) of the fiducial mark is obtained.

The deconvolution operation unit 73 carries out the deconvolution operation on the profile data in the Y direction, similar to the deconvolution operation performed on the profile data in the X direction stated above. The deconvolution operation unit 73 carries out the deconvolution operation on $[P_{X1}(y), P_{X2}(y), P_{X3}(y) \ldots]$ using a common LSF(y). It is therefore possible to generate one-dimensional (Y direction) deconvolution operation data for each X direction position. Then, by synthesizing the plurality of pieces of deconvolution operation data, the two-dimensional deconvoluted image is generated. By detecting the edges of the fiducial mark, the coordinate calculation unit 74 detects the Y coordinate of the fiducial mark in the image.

The coordinate calculation unit 74 obtains, for example, in each X coordinate (X1, X2, X3 . . . ), the central position of the edges of the cross-shaped fiducial mark as the edge coordinates. Then the midpoint of the coordinates of the two upper and lower edges 23a is set to be the Y coordinates ($E_{X1}, E_{X2}, E_{X3}$ . . . ) of the fiducial mark in each X coordinate. Then the average value of the Y coordinates ($E_{x1}, E_{x2}, E_{x3}$ . . . ) of the fiducial mark in the plurality of X coordinates is set to be the Y coordinate of the fiducial mark. In this way, the Y direction position (Y coordinate) of the fiducial mark is obtained.

As described above, in this embodiment, the deconvolution operation unit 73 carries out the one-dimensional deconvolution operation using the line spread function. It is therefore possible to generate the deconvolution operation data in which the distortion of the edges is corrected. By using the deconvolution operation data, the XY coordinates (central coordinates) of the fiducial mark can be accurately detected.

According to the above operation, the coordinates of the fiducial mark can be detected with high repeatability. It is therefore possible to accurately detect the coordinates of the defect. Even when the image in the focus position deviated from an optimum focal plane is acquired, for example, the distortion of the edges can be corrected by the point spread function. It is therefore possible to increase the accuracy of detecting the coordinates.

In the following description, one example of the coordinate detection method according to this embodiment will be described. First, data of the point spread function in which the characteristics of the measuring optical system are expressed is prepared in advance. The fiducial mark is then captured and a predetermined area of the edge part is set to be an area to be processed. Then the one-dimensional deconvolution operation is carried out on the profile data of the vertical direction of the edges. It is therefore possible to correct the profile data. The deconvolution operation on the profile data is carried out for all the pixel positions of the horizontal direction of the edges.

The profile data that is corrected is assembled side by side to form a two-dimensional image. The central position of the edges of the assembled edge image is obtained. The vertical and horizontal edges of the fiducial mark are processed in a similar way to obtain the line segment between the center of the edges opposed to each other in the vertical direction and the center of the edges opposed to each other in the horizontal direction. The intersection of the line segment in the vertical direction and the line segment in the horizontal direction can be set to be the central coordinates of the fiducial mark. According to this operation, it is possible to detect the coordinates with high repeatability. Even when the image is blurred, the coordinates can be accurately detected.

Further, the profile data generation unit 75 generates the Y-direction profile data in the plurality of X coordinates. The deconvolution operation unit 73 carries out the one-dimensional deconvolution operation for each of the pieces of the Y-direction profile data. The coordinate calculation unit 74 detects the Y coordinate of the fiducial mark based on the plurality of deconvolution operation results. It is therefore possible to accurately detect the Y coordinate. Similarly, the profile data generation unit 75 generates the X-direction profile data for each Y coordinate. The deconvolution operation unit 73 carries out the one-dimensional deconvolution operation for each of the pieces of the X-direction profile data. The coordinate calculation unit 74 detects the X coordinate of the fiducial mark based on the plurality of deconvolution operation results. It is therefore possible to accurately detect the X coordinate. It is therefore possible to accurately detect the XY coordinates. Further, since the deconvolution operation unit 73 carries out the one-dimensional deconvolution operation, there is no need to carry out the two-dimensional deconvolution operation. Therefore, the processing can be simplified.

While the example of detecting the coordinates of the fiducial mark has been described in the third and fourth embodiments, the present invention may be applied to the detection of the coordinates of an arbitrary pattern provided in the sample. That is, it is possible to acquire the positional information of the pattern that can be captured by the image capture unit. The coordinate detection apparatus according to this embodiment may also be applied, for example, to a specification of the position of the defect. Further, the present invention can also be applied to an application that specifies the position of the mask pattern to perform matching. Further, in the fourth embodiment, it is possible to detect the coordinates of the pattern having linear edges.

Each of the above-described embodiments can be combined as desirable by one of ordinary skill in the art.

The processing apparatus can execute the above process by executing a computer program. The program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g., magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g., electric wires, and optical fibers) or a wireless communication line.

While the embodiments of the present invention have been described above, the present invention includes various modifications without impairing the objects and the advantages and is not limited to the embodiments stated above.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

The invention claimed is:

1. An inspection apparatus comprising:
   an illumination light source that generates illumination light, the illumination light illuminating a sample;
   an image capture unit that captures a plurality of images of the sample in different focus positions in an optical axis direction; and
   a processing apparatus that generates an image in a desired focus position in the optical axis direction based on the plurality of images, wherein the processing apparatus comprises:
   a profile data generation unit that divides each of the plurality of images according to a circumferential position to generate profile data in which a radial direction position and luminance data are associated with each other;
a deconvolution operation unit that carries out a deconvolution operation using a one-dimensional point spread function to generate deconvolution operation data based on the profile data;
an estimation unit that estimates estimation data of the deconvolution operation data in the desired focus position in the optical axis direction using the deconvolution operation data; and
a synthesis unit that synthesizes the estimation data estimated by the estimation unit for each radial direction position to generate the image in the desired focus position.

2. The inspection apparatus according to claim 1, wherein:
the processing apparatus calculates a shift amount of a peak position of the deconvolution operation data or the profile data, and
the estimation unit shifts the deconvolution operation data in a radial direction based on the shift amount to estimate the estimation data.

3. The inspection apparatus according to claim 2, comprising:
carrying out, by the deconvolution operation unit, the deconvolution operation on the profile data at each of the different focus positions to generate a plurality of pieces of deconvolution operation data;
calculating a peak position of each of the plurality of pieces of deconvolution operation data; and
shifting the deconvolution operation data in the radial direction based on the shift amount of the peak position of each of the plurality of pieces of deconvolution operation data to calculate the estimation data.

4. The inspection apparatus according to claim 2, comprising:
carrying out a convolution operation using two pieces of profile data having different focus positions to generate convolution operation data;
obtaining a shift amount of a peak position of each of the two pieces of profile data based on the convolution operation data;
shifting one of the two pieces of profile data in the radial direction based on the shift amount; and
carrying out, by the deconvolution operation unit, the deconvolution operation on the square root of the product of one piece of the profile data shifted in the radial direction and the other pieces of profile data to generate the deconvolution operation data.

5. The inspection apparatus according to claim 1, wherein at least one curved mirror is provided in an optical system that propagates scattered light from the sample to the image capture unit and the curved mirror projects the sample on the image capture unit in a magnified manner.

6. The inspection apparatus according to claim 1, wherein the illumination light is EUV light.

7. A wavefront aberration correction method in which a processing apparatus generates an image in a desired focus position in an optical axis direction based on a plurality of images captured in different focus positions in the optical axis direction, wherein the step of generating the image comprises:
dividing each of the plurality of images according to a circumferential position to generate profile data in which a radial direction position and luminance data are associated with each other;
carrying out a deconvolution operation using a one-dimensional point spread function to generate deconvolution operation data based on the profile data;
estimating estimation data of the deconvolution operation data in the desired focus position in the optical axis direction using the deconvolution operation data; and
synthesizing the estimation data for each radial direction position to generate the image in the desired focus position.

8. The wavefront aberration correction method according to claim 7, comprising:
calculating a shift amount of a peak position of the deconvolution operation data or the profile data; and
shifting the deconvolution operation data in a radial direction based on the peak position to estimate the estimation data.

9. The wavefront aberration correction method according to claim 8, comprising:
carrying out the deconvolution operation on the profile data at each of the different focus positions to generate a plurality of pieces of deconvolution operation data;
calculating a peak position of each of the plurality of pieces of deconvolution operation data; and
shifting the deconvolution operation data in the radial direction based on the shift amount of the peak position of each of the plurality of pieces of deconvolution operation data to calculate the estimation data.

10. The wavefront aberration correction method according to claim 8, comprising:
carrying out a convolution operation using two pieces of profile data having different focus positions to generate convolution operation data;
obtaining a shift amount of a peak position of each of the two pieces of profile data based on the convolution operation data;
shifting one of the two pieces of profile data in the radial direction based on the shift amount; and
carrying out, by a deconvolution operation unit, the deconvolution operation on the square root of the product of one piece of the profile data shifted in the radial direction and the other pieces of profile data to generate the deconvolution operation data.

11. The wavefront aberration correction method according to claim 7, wherein at least one curved mirror is provided in an optical system that propagates scattered light from a sample to an image capture unit and the curved mirror projects the sample on the image capture unit in a magnified manner.

12. The wavefront aberration correction method according to claim 7, wherein illumination light that illuminates a sample is EUV light.

* * * * *